US010733726B2

(12) United States Patent
Lloyd et al.

(10) Patent No.: US 10,733,726 B2
(45) Date of Patent: Aug. 4, 2020

(54) PATHOLOGY CASE REVIEW, ANALYSIS AND PREDICTION

(71) Applicant: H. LEE MOFFITT CANCER CENTER AND RESEARCH INSTITUTE, INC., Tampa, FL (US)

(72) Inventors: Mark Cassidy Cridlin Lloyd, Tampa, FL (US); Marilyn Yuanxin Ma Bui, Tampa, FL (US); Katarzyna Ann Rejniak, Tampa, FL (US); Munish Puri, Tampa, FL (US)

(73) Assignee: H LEE MOFFITT CANCER CENTER AND RESEARCH INSTITUTE, Tampa, FL (US)

( * ) Notice: Subject to any disclaimer, the term of this patent is extended or adjusted under 35 U.S.C. 154(b) by 105 days.

(21) Appl. No.: 16/029,761

(22) Filed: Jul. 9, 2018

(65) Prior Publication Data
US 2019/0087954 A1 Mar. 21, 2019

Related U.S. Application Data

(63) Continuation of application No. 15/034,683, filed as application No. PCT/US2014/064221 on Nov. 6, 2014, now Pat. No. 10,049,447.
(Continued)

(51) Int. Cl.
*G06K 9/00* (2006.01)
*G06T 7/00* (2017.01)
(Continued)

(52) U.S. Cl.
CPC .......... *G06T 7/0012* (2013.01); *G06K 9/0014* (2013.01); *G06K 9/00147* (2013.01);
(Continued)

(58) Field of Classification Search
CPC ........... G06K 2209/051; G06K 9/0014; G06K 9/00147; G06K 9/4604; G06K 9/6267;
(Continued)

(56) References Cited

U.S. PATENT DOCUMENTS 7,761,240 B2 * 7/2010 Saidi .................... G06K 9/0014
382/128
2008/0015448 A1 * 1/2008 Keely .................. A61B 5/0091
600/477

(Continued)

*Primary Examiner* — Ian L Lemieux
(74) *Attorney, Agent, or Firm* — Meunier Carlin & Curfman LLC

(57) ABSTRACT

Systems and methods for personalized cancer therapy using analysis of pathology slides to target regions in a single sample that interrogates the feature data of a relatively large number of cells. The disclosure describes pathology case review tools of the future which include analysis, visualization and prediction modeling to provide novel information to the pathologist for the diagnosis of disease. This disclosure further describes a user interface to assist the physicians that make that diagnosis, pathologists. Complex computer learning algorithms will combine and mine these data sets to recommend optimal treatment strategies. A computer interface is provided which allows a pathologist to access those data instantly to make a more informed and accurate diagnosis.

20 Claims, 22 Drawing Sheets

Related U.S. Application Data

(60) Provisional application No. 61/900,711, filed on Nov. 6, 2013, provisional application No. 61/900,716, filed on Nov. 6, 2013, provisional application No. 61/900,719, filed on Nov. 6, 2013, provisional application No. 61/900,723, filed on Nov. 6, 2013.

(51) Int. Cl.
    *G06T 7/11* (2017.01)
    *G06K 9/46* (2006.01)
    *G06K 9/62* (2006.01)
    *G16H 50/20* (2018.01)

(52) U.S. Cl.
    CPC ......... *G06K 9/4604* (2013.01); *G06K 9/6267* (2013.01); *G06T 7/11* (2017.01); *G06K 2209/051* (2013.01); *G06T 2207/10056* (2013.01); *G06T 2207/20081* (2013.01); *G06T 2207/30024* (2013.01); *G06T 2207/30096* (2013.01); *G16H 50/20* (2018.01)

(58) Field of Classification Search
    CPC . G06T 2207/10056; G06T 2207/20081; G06T 2207/30024; G06T 2207/30096; G06T 7/0012; G06T 7/11; G16H 50/20
    See application file for complete search history.

(56) References Cited

U.S. PATENT DOCUMENTS

| | | | |
|---|---|---|---|
| 2010/0185064 A1* | 7/2010 | Bandic | A61B 5/0059 600/306 |
| 2010/0254589 A1* | 10/2010 | Gallagher | G06K 9/0014 382/133 |
| 2011/0243417 A1* | 10/2011 | Madabhushi | G06K 9/3233 382/131 |
| 2011/0301441 A1* | 12/2011 | Bandic | A61B 5/0059 600/306 |
| 2012/0321759 A1* | 12/2012 | Marinkovich | A61B 5/0531 426/231 |
| 2013/0080134 A1* | 3/2013 | Donovan | G06N 7/005 703/11 |
| 2014/0233826 A1* | 8/2014 | Agaian | G06K 9/46 382/133 |
| 2015/0049081 A1* | 2/2015 | Coffey | G06T 19/006 345/419 |
| 2016/0131569 A1* | 5/2016 | Mai | G01N 15/1475 382/128 |
| 2016/0203599 A1* | 7/2016 | Gillies | A61B 6/463 382/132 |
| 2016/0266126 A1* | 9/2016 | Shipitsin | C12Q 1/6886 |
| 2017/0270666 A1* | 9/2017 | Barnes | G16H 50/30 |
| 2018/0253841 A1* | 9/2018 | Madabhushi | G06T 7/0012 |
| 2019/0072559 A1* | 3/2019 | Gu | C07D 209/24 |
| 2019/0113423 A1* | 4/2019 | Goodman | G01N 33/4833 |
| 2020/0024669 A1* | 1/2020 | Spetzler | C12Q 1/6886 |
| 2020/0075169 A1* | 3/2020 | Lau | G16B 25/10 |

* cited by examiner

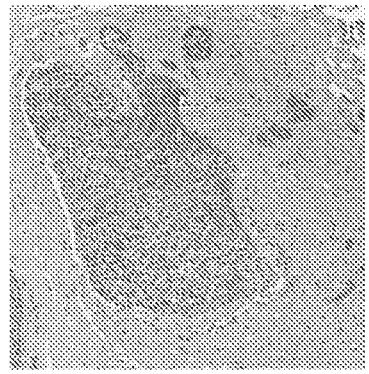
*FIG. 16A*
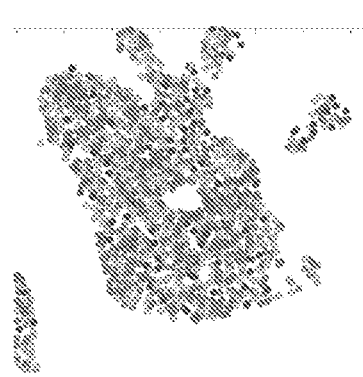 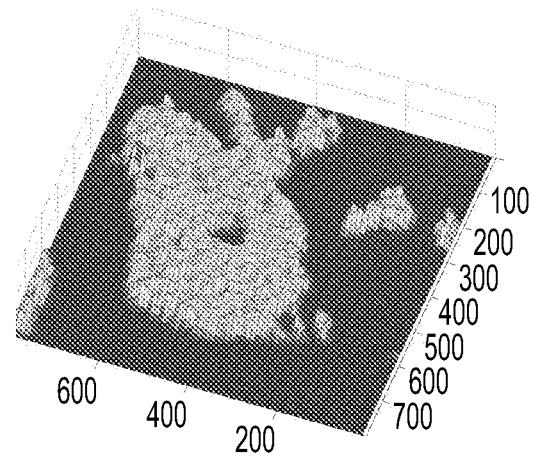
*FIG. 16B*   *FIG. 16C*

PATHOLOGY CASE REVIEW, ANALYSIS AND PREDICTION

CROSS-REFERENCE TO RELATED APPLICATIONS

This application is a continuation of U.S. patent application Ser. No. 15/034,683, filed May 5, 2016, which is a 35 U.S.C. § 371 National Phase filing of PCT/US2014/64221, filed Nov. 6, 2014, which claims the benefit of priority to U.S. Provisional Application No. 61/900,711, filed Nov. 6, 2013; U.S. Provisional Application No. 61/900,716, filed Nov. 6, 2013; U.S. Provisional Application No. 61/900,719, filed Nov. 6, 2013; and U.S. Provisional Application No. 61/900,723, filed Nov. 6, 2013, each of which is hereby incorporated by reference herein in its entirety.

STATEMENT REGARDING FEDERALLY FUNDED RESEARCH

This invention was made with Government support under Grant Nos. CA076292 and CA143970 awarded by the National Institutes of Health (NIH) and W81XWH-08-2-0101 awarded by the US Army Medical Materiel (ARMY/MRMC). The Government has certain rights in the invention.

BACKGROUND

Personalized medicine aims to take a targeted approach to cancer therapy to best design the optimal therapy for each individual patient. Massive biobanks of patient tissues are being constructed to create extensive libraries of genetic data on large numbers of cancers for correlation with targeted therapies. However, discriminating and cataloguing genomic libraries of patient samples is complex because of factors related to tissue region and cellular variation.

SUMMARY

The present disclosure describes systems and methods for personalized cancer therapy, using analysis of pathology slides to target regions in a single sample that interrogates the feature data of a relatively large number of cells. Complex training and visualization can be used to spatial identify tumor variation. The disclosure describes pathology case review tools of the future which include analysis, visualization and prediction modeling to provide novel information to the pathologist for the diagnosis of disease. This disclosure further describes a user interface to assist the physicians that make that diagnosis, pathologists. The 'Pathology Case Review of the Future' takes advantage of the immense data embedded in medical images by isolating, extracting and data basing valuable information about complex cancers. Complex computer learning algorithms will combine and mine these data sets to recommend optimal treatment strategies much like hurricane models (spaghetti plots) predict the paths a storm may take. A computer interface is provided which allows a pathologist to access those data instantly to make a more informed and accurate diagnosis. The present disclosure seeks to offer a better diagnosis; which will lead to a better outcome.

It is generally accepted that genetic heterogeneity among cancer cells is a manifestation of intratumoral evolution, and this is typically viewed as a consequence of random mutations generated by genomic instability within the cancer cells. While current imaging technologies are useful to identify the physiological heterogeneity in tumors, they are not nearly as useful as they could be. We propose that optimized use of these technologies can better define the cellular and environmental heterogeneity that exist in individual tumors; and that this requires more robust and more quantitative analyses of images.

Typically, patients have pathological samples during the diagnostic process. This provides an enormous untapped wealth of information about biological variability in individual cancers. Pathologic feature analysis can provide precise information regarding regional variations in environmental selection forces and phenotypic adaptations. These observations can be integrated using quantitative, spatially-explicit methods developed in ecology to define the underlying heterogeneous biological processes in tumors within individual patients. These images can reveal regional variations of the ecological and evolutionary forces that govern tumor growth, metastases, therapy response and, ultimately, the clinical course, outcome and survival. This vast amount of untapped data can ultimately lead to the development of more accurately direct therapeutic options for individual patients.

Heterogeneity among cancer cells has long been recognized as a property of cancer progression and resistance to therapeutic intervention. The described heterogeneous responses to the tumor microenvironment can create the chaotic and seemingly incomprehensible nature of cancer which is only within the last few years becoming fully appreciated. Below is a description of how multiparametric morphological features of single cells in histology sections and can be used to design informative decision making tools for pathologists.

An optical microscopy digitization based approach is used to collect individual phenotypic cell feature data of whole slides and integrate co-matrix data analysis tools in conjunction with neural network analysis. Complex computer engineered analysis and modeling is used to investigate morphological heterogeneity within the histology of tumor and its physical microenvironment can be interrogated and provide information which can be used as companion diagnostics for pathologists.

Molecular analysis from populations of cells (either a whole tumor or small biopsy of that tumor) is, at best, an incomplete representation of the underlying biology. These observations indicate a significant need to define intratumoral spatial variations in cellular properties. Variation in tumor morphology is being recognized as a novel tool to compliment genetic and epigenetic methods to investigate somatic evolution in breast cancer. Histological image analysis can be used to objectively quantify tumor morphology, molecular expression, and spatial considerations in a cumulative manner, which in beginning to be used as a digital tool to supplement current standards of predicting prognosis.

Quantitative morphometric signatures and understanding the spatial arrangements of tumor cell phenotype inform tumor progression and its relationship with its local physical microenvironment (PME). Physical features of the benign, malignant tumor and PME can be used to evaluate cancer progression by 1) identifying clusters of cell subpopulations with like phenotypes which may demonstrate a genetic basis of predictable changes and; 17) illuminating the link between these phenotypic changes and tumor progression which; 3) are correlated to changes in the pliable nature of the PME which promotes distinct niche filling by evolving tumor cells that adapt to diverse opportunities. Morphometric features such as increased nuclear size, nuclear contents and anomalous chromatin texture can be utilized for early cancer detection and accurate scoring. Nuclear pleomorphism investigation through the mutator phenotype theory of carcinogenesis, nuclear chromatin binding and internal nuclear mutations can elucidate a better understanding towards developing novel automated prognostic tools.

Here, morphometric features of sets of cancer cells and subpopulations to identify clusters of similar phenotypes. Map with multiple layers the locations of vasculature, inflammation and additional stromal components including collagen arrangement and cancer associated fibroblasts can be generated. This information can be linked to breast cancer progression using cases of various pathology grade (i.e. Nottingham score in breast) to identify trends.

Nottingham score, for example, is a well-established microscopic grading of breast cancer and is associated with survival of breast cancer patients, however several groups contend that pathologic evaluation alone does not provide enough information to be an ideal prognostic indicator. In order to produce a more accurate prediction of prognosis and response to therapy, there is a need to develop a more quantifiable method for automated image cytometry and hypsometry.

Image analysis is an optimal way to evaluate multiparametric features which are not visible to the eye which therefore induces errors and inaccurate prognoses. Understanding the heterogeneity of the tumor, the genetic instability of carcinogenesis and related PME (e.g. niches, adaptive strategies) can be useful in creating a computational tool for companion diagnostics. Pathologists could improve their ability to accurately evaluate cancer grading and therapeutics with companion diagnostic tools capable of adding valuable information to their decision making process.

An interface for the Pathology Case Review of the Future can be available on a monitor and in real time. It will be the resultant of processing glass microscope slides to create a digital image and then extract and computationally process the results to offer a prediction which enhances the pathologist's means to support their patients.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views:

FIGS. 16A-16G illustrate inputs to, and outputs of, the operational flow of FIG. 15 and illustrate a hematoxylin and eosin (H&E) stained histology slide and its associated landscape outputs.

DETAILED DESCRIPTION

Figure 1:
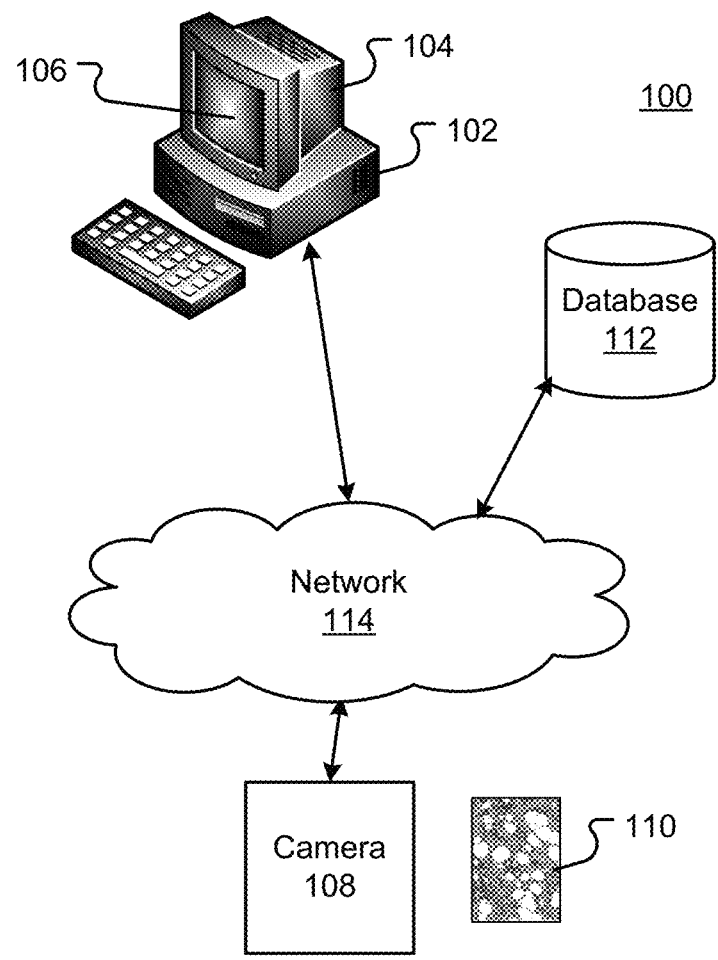
FIG. 1 illustrates an exemplary environment.

Spatial Region Identification within Digital Image Analysis

Overview

The present disclosure describes systems and methods for personalized cancer therapy, using genetic analysis for target lesions in a single sample that averages the genomes of a relatively large number of cells are not optimal. As will be described below, cancer tumors can be understood by characterizing their underlying evolutionary dynamics, including both spatially and temporally variability. While pathologists may evaluate variability across histological samples visually, there are challenges to doing so algorithmically. The challenges are threefold, as identification of cellular variation should be regionally explicit, quantitative and reproducible, and have high throughput. With the advent of whole slide imaging technology and recent improvements in pattern recognition software, it is possible to computationally evaluate millions of cells in minutes and hundreds of patients in hours to days. Whole slide imaging allows high resolution and high throughput image acquisition for every cell within a given tissue sample. There are a number of advantages of these technologies including low costs, high throughputs, quantitative results and rapid dissemination among tissue samples. The present disclosure extends pathology to identify, classify and quantify these variation to supplement the current efforts of personalized medicine. Analysis of histological samples within a spatial context may be investigated by employing the theories, tools and experience of digital pathology.

Intratumoral variation manifests in at least three general ways. A first is a mixture or normal and malignant cellular populations within tissue. Pathologists typically describe this variation in qualitative terms. The pathologist will, for example, recognize benign cells such as fibroblasts, lymphocytic and epithelial cells, et cetera. They will also identify abnormal phenomena such as inflammation, necrosis, hyperplasia, pre-neoplastic disease, benign tumors and malignant neoplasms, i.e., cancers. In current practice, pathologists attempt to overcome this variation by selecting regions of tissues for genetic analysis that minimizes normal or necrotic cells.

Term Definitions

As used herein, the following terms have the following meanings:

Sample: includes cellular material derived from a biological organism.

Tissue: refers to a mass of connected cells (e.g., central nervous system (CNS) tissue, neural tissue, or eye tissue) derived from a human or other animal and includes the connecting material and the liquid material in association with the cells.

Biological component: includes, but is not limited to nucleus, cytoplasm, membrane, epithelium, and nucleolus and stromal.

Medical diagnosis: includes analysis and interpretation of the state of tissue material.

Objects: A space or shape with a defined border

SubObjects: a space or shape inside a defined object with its own defined border Object Feature Data: A distinct attribute of an object which is quantified with a discrete or continuous value Classification: Categorical and quantitative qualities of a feature, characteristic or group of features or characteristics Multiparametric Feature Data: A collection of specific quantitative metrics, spatial, geometric or otherwise which are grouped Spatial Model: A system used to imitate object interaction and progression over time, relative to space.

Model Prediction: A method to evaluation outcome probability with a given model system Rugosity: A metric of complexity, diversity and variation Complexity: Level of intricate parts, elements or features involved in object relationships Diversity: Quality or state of being different in time, space, genetics, morphology or other characteristics Analytics: Data and statistics with spatial, arithmetic or geometric value Microenvironment: The conditions surrounding tumor regions including, but not limited to, vasculature, collagen arrangement, inflammatory response et cetera Example Digital Pathology Environment Digital pathology is the concept of capturing digital images from glass microscope slides in order to record, visualize, analyze, manage, report, share and diagnose pathology specimens. This practice is being integrated in pathology departments to increase productivity, workflow efficiency and the ability to quantify results. In particular, slide scanners automate repeatable imaging conditions for whole slides. As will be described herein below, the present disclosure provides implementations of a desktop single slide scanner that, e.g., will enable pathologists to scan slides at a touch of a button. Furthermore, when integrated with specialized software tools, pathologists may establish a one-stop workflow for reliable imaging, diagnosis, quantification, management, and sharing of their own digital pathology library.

FIG. 1 is a block diagram illustrating an exemplary automated digital image based biological sample feature detection and classification system 100. The system 100 may include one or more computers 102 with a computer display 104 (only one of which is illustrated). The computer display 104 may present a graphical user interface ("GUI") 106 to a user. The system 100 may optionally include a microscope or other magnifying device (not illustrated). The system 100 further includes a digital or analog camera 108 used to provide plural images 110 in various image or data formats. Although not shown, a slide scanner may be used in conjunction with the camera 108.

One or more databases 112 may store biological sample information as digital images or in other digital data formats. The one or more database 112 may also include raw and/or processed digital images and may further include knowledge databases created from automated analysis of the digital images 110. The one or more databases 112 may be integral to a memory system on the computer 102 or in secondary storage such as a hard disk, solid state media, optical disk, or other non-volatile mass storage devices. The computer 102 and the databases 112 may also be connected to an accessible via one or more communications networks 114 and/or distributed across components connected to the communications networks 114. All memory systems and computer-readable media disclosed herein are intended to be tangible memory systems.

Figure 21:
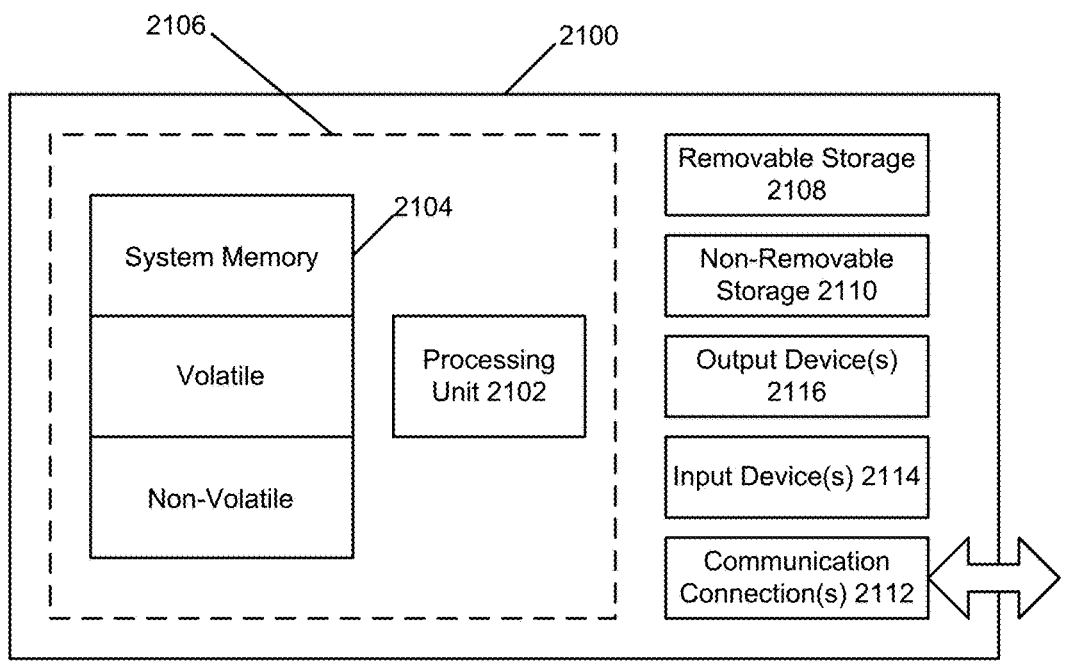
FIG. 21 shows an example computing environment.

In the above system 100, the one or more computers 102 include, but are not limited to desktop computers, laptop/notebook computers, workstations, thin clients, mobile devices, tablet computers, smart phones, personal digital assistants (PDA), Internet appliances, etc. An example computing device is shown in FIG. 21.

The communications network 114 may include, but is not limited to, the Internet, an intranet, a wired or wireless Local Area Network (LAN or WiLAN), a Wide Area Network (WAN), a Metropolitan Area Network (MAN), Public Switched Telephone Network (PSTN) and other types of communications networks 114. The communications network 114 may include one or more gateways, routers, or bridges. The communications network 114 may include one or more servers and one or more web-sites accessible by users to send and receive information useable by the one or more computers 102. The communications network 114 includes, but is not limited to, data networks using the Transmission Control Protocol (TCP), User Datagram Protocol (UDP), Internet Protocol (IP) and other data protocols.

The one or more databases 112 may include plural digital images 110 of biological samples taken with a camera such as a digital camera and stored in a variety of digital image formats including, but not limited to, TIFF (without compression). However, the present disclosure is not limited to these digital image formats and other digital image or digital data formats can also be used to practice the subject matter of the disclosure. The digital images 110 are typically obtained by magnifying the biological samples with a microscope or other magnifying device and capturing a digital image of the magnified biological sample.

Each digital image 110 typically includes an array, usually a rectangular matrix, of pixels. Each "pixel" is one picture element and is a digital quantity that is a value that represents some property of the image at a location in the array corresponding to a particular location in the image. Typically, in continuous tone black and white images the pixel values represent a gray scale value. Pixel values for a digital image 110 typically conform to a specified range. For example, each array element may be one byte (i.e., eight bits). With one-byte pixels, pixel values range from zero to 255. In a gray scale image a 255 may represent absolute white and zero total black (or visa-versa). Color digital images consist of three color planes, generally corresponding to red, green, and blue (RGB). For a particular pixel, there is one value for each of these color planes, (i.e., a value representing the red component, a value representing the green component, and a value representing the blue component). By varying the intensity of these three components, all colors in the color spectrum typically may be created.

Data may be maintained on a tangible computer readable medium including magnetic disks, solid state media, optical disks, organic memory, and any other volatile (e.g., Random Access Memory ("RAM")) or non-volatile (e.g., Read-Only Memory ("ROM"), flash memory, etc.) mass storage system readable by the CPU. The computer readable medium includes cooperating or interconnected computer readable medium, which exist exclusively on the processing system or can be distributed among multiple interconnected processing systems that may be local or remote to the processing system.

As will be described in detail below, digital images 110 representing biological samples including cells, tissue samples, etc may be analyzed to provide a determination of certain known medical conditions for humans and animals. For example, digital images 110 may be used to determine cell proliferate disorders such as cancers, etc. in humans and animals. Digital images 110 may be captured by, e.g., cameras 108 provided in optical microscopes, where the digital images 110 represent the images seen by a human eye through the microscope. The images may then be stored in the one or more databases 112.

Spatial Region Identification within Digital Image Analysis

Histology pattern recognition utilizes complex computer learning models which are trained by, e.g., a pathologist. By teaching the algorithm to recognize the same regions described above, a computer can reliably identify the regions of interest in a robust and repeatable way. Individual physical or molecular features derived from the images can be used to catalog populations and relationships between cells or regions and establish testable hypotheses to further interrogate processes of the system. This also creates and thus defines a border between tissue regions. Qualitatively, the regions of interest could then be evaluated. With these tools precise metrics of the regions can be quantified. Initially these metrics might include area, intensity, roundness and other physical features. These regional tissue features can also be quantitatively measured and used to evaluate the disease at a regional scale. Once distinctive environmental regions are identified, the morphological or phenotypic properties of individual cells within that region can be evaluated. In turn, this enables the intratumoral variation to be characterized, quantified and ultimately compared.

The present disclosure provides a method for, e.g., pathologists to define the dynamics within cancers through application of methods of quantitative identification and classification analysis of tumor histology. Spatial variation in these tissues can be measured and used to define both prognosis and optimal therapeutic strategies.

Figure 2:
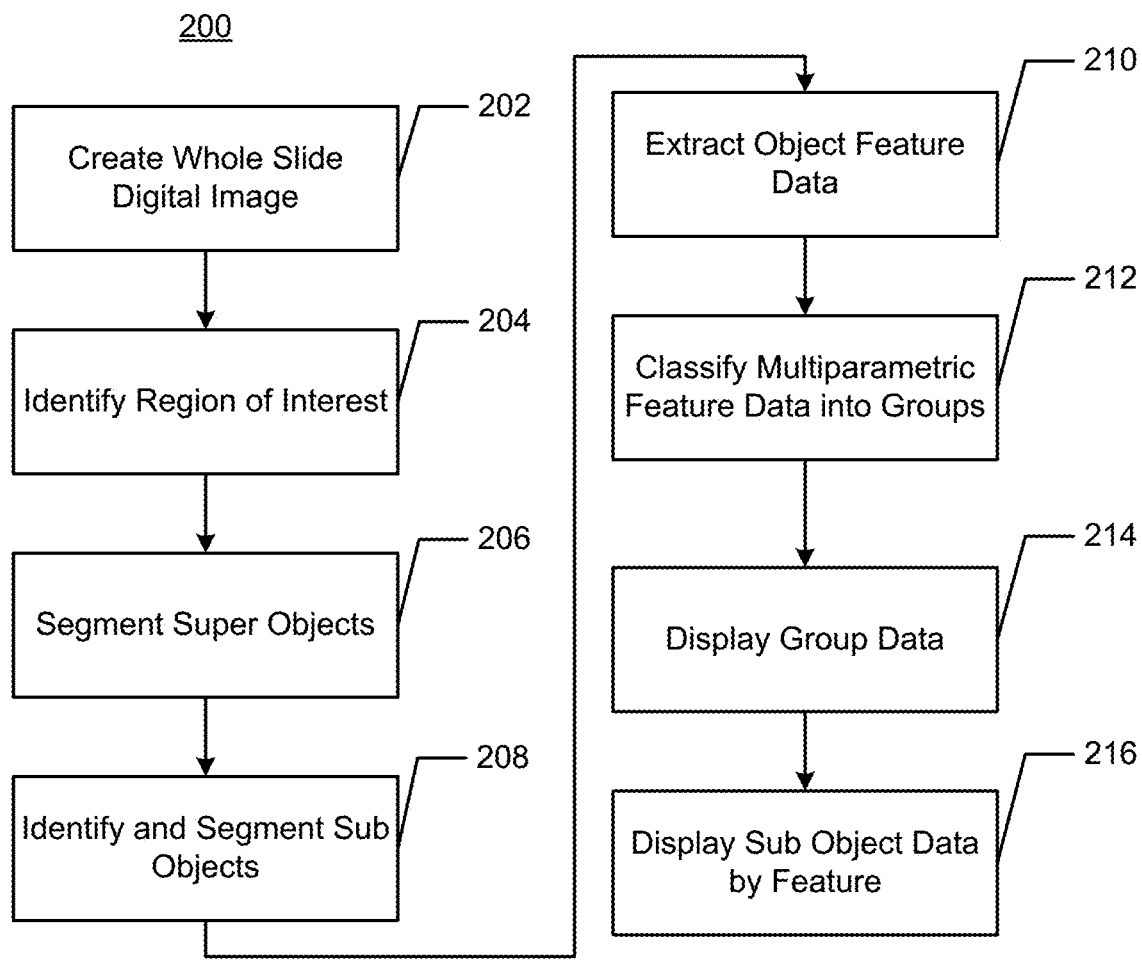
FIG. 2 illustrates an example operational flow.

FIG. 2 illustrates an example operational flow 200 in accordance with present disclosure wherein visualizations of features of digital images are generated from image data. As will be described below, using digitized slides, cell feature data may be identified and displayed to provide a visualization of certain characteristics of tumor cells.

At 202, a whole slide image is obtained. This may be a digitization of a glass microscope slide at a level of resolution suitable to make a diagnosis. For example, this may be 200× magnification at a resolution of 0.5 μm/pixel. The digitization of the glass slide may be performed using equipment such as an Aperio AT ScanScope, available from Aperio, Vista, Calif.

At 204, regions of interest are identified. For example, non-tumor regions may be segmented from tumor regions. The identification may be performed manually by a pathologist using, e.g., a pen or a pointing device. The identification may be performed automatically by a computing device using, e.g., pattern recognition or other techniques. Areas such as fat, skin, muscles, bone around a tumor may be identified. Abnormal tissue area, such as hyperplastic or pre-lesion areas may be identified. As a result, an invasive cancer can be segmented.

Figure 3:
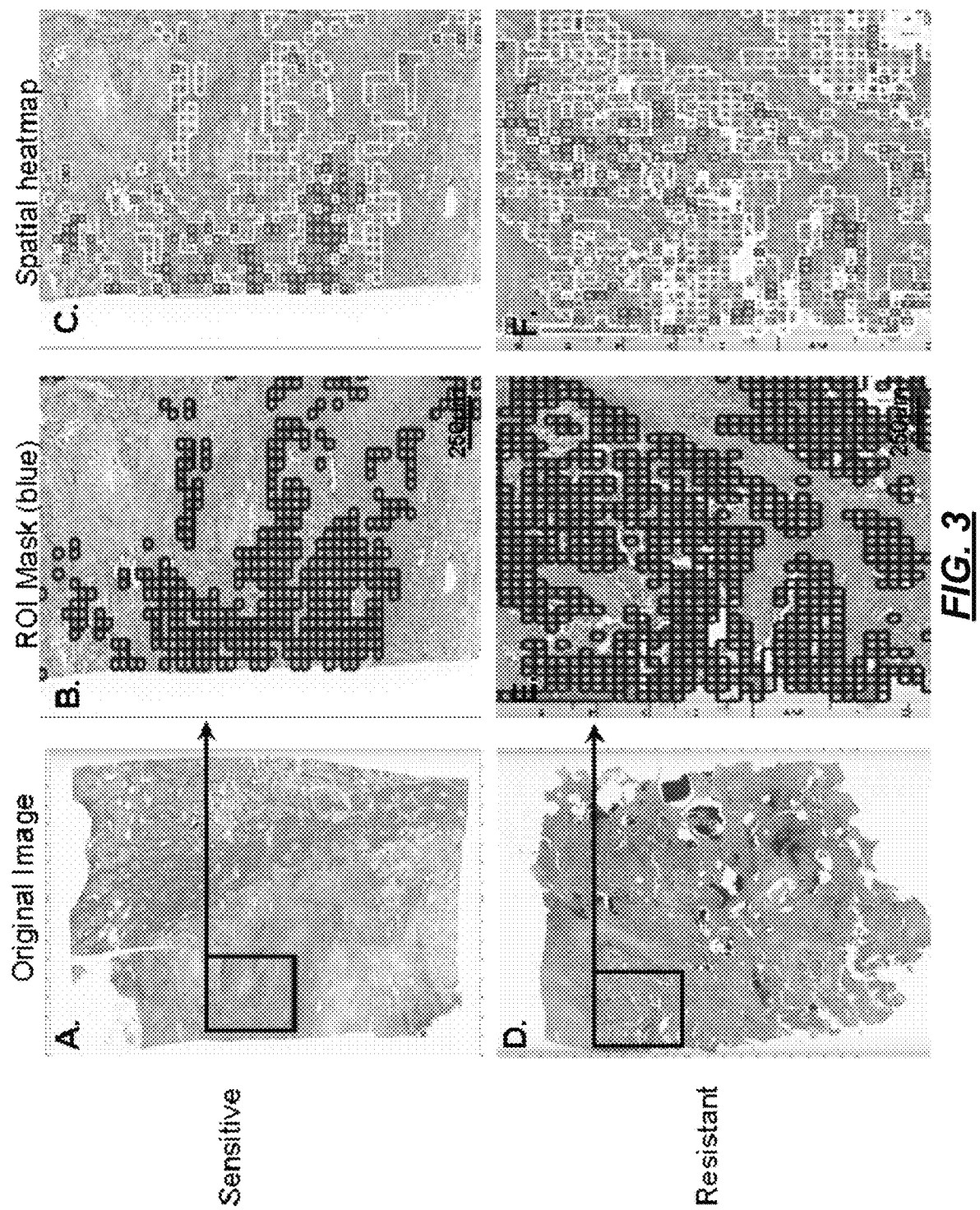
FIGS. 3-4 illustrate outputs of the operational flow of FIG. 2.

At 206, "super objects" may be segmented. As used herein, "super objects" are "higher-level" objects that are larger than the smallest objects of interest (e.g., cells). Referring to FIG. 3, there are illustrated two digital slides samples. One is of a sensitive region (FIG. 3A) that is responsive to treatment, and the other of a resistant region (FIG. 3D) that is not responsive to treatment. The super objects may be identified by superimposing a checkerboard over the image, where the checkerboard has like size squares, as shown in FIG. 3B and FIG. 3E. In some implementations, the super objects may be identified using spectral separation to classify the image by color or density. Architectures may also be examined to identify, e.g., blood vessels within a sample.

At 208, "subobjects" are identified and segmented. For example, the subobjects may be the smallest object of interest, such as cells or cell nuclei. The subobjects may each be identified and segmented separately such that every cell may be a subobject. The subobjects may be identified using software pattern recognition techniques. For example, imaging solutions available from Visiopharm may be used for this purpose.

At 210, object feature data is extracted from the image in accordance with the identified subobjects. The feature data will represents parameters associated with the subobject. For example, the feature data may be one (or more) of the follow non-limiting example features:

| | | | |
|---|---|---|---|
| Skewness | Rel Border to Brighter Neighbors | Density | ZCenter |
| Layer Values | | Elliptic Fit | ZMax |
| Pixel Based Ratio | | Radius of Largest Enclosed Ellipse | Z Min |
| Min Pixel Value | To Superobject | | Feature Value Range |
| Max Pixel Value | Mean Diff to Superobject | | |
| Mean of Inner Border | Ratio to Superobject | Radius of Smallest Enclosing Ellipse | Object Features: |
| Mean of Outer Border | Std Dev Diff to Superobject | Rectangular Fit | Texture Layer Value |
| Contrast to Neighbor Pixels | Std Dev Ratio to Superobject | Roundness | Texture Based on Sub-objects |
| Edge Contrast of Neighbor Pixels | Hue | Shape Index | Mean of Sub-objects:Std Dev |
| Std Dev to Neighbor Pixels | Saturation Intensity | Degree of Skeleton Branching | Avrg Mean Diff to Neighbors of Sub-objects |
| Circular Mean | HIS Transformation | Length of MainLine | |
| Circular Std Dev | Object Features: | Length/Width | Shape Texture |
| Circular Std Dev/Mean To Neighbors | Geometry Extent | Maximum Branch Length | Based on Sub-objects |
| Mean Diff to Neighbors | Area Border Length | Number of Segments | Area of Sub-objects: Mean |
| Mean Diff to Neighbors (Abs) | Border Length Length | Std dev Curvature | Area of Sub-objects: |
| Mean Diff to Darker Neighbors | Length/Thickness Length/Width Number of | Std dev of Area Represented by Segments Distance Distance to Line | Std Dev Density of Sub-objects: Mean Density of Sub- |

| | | | |
|---|---|---|---|
| Mean Diff to Brighter Neighbors | Pixels Thickness Volume | Distance to Anything Co-ordinate | objects: Std Dev Asymmetry of |
| Number of Brighter Objects | Width Shape | X Center X Max | Sub-objects: Mean |
| Number of Darker Objects | Asymmetry Border Index Compactness | X Min Y Center YMax YMin | Asymmetry of Sub-objects: Std Dev Direction of Sub-objects: Mean |

The feature data associated with each of the subobjects may be stored in an array, for example, where each row represents a particular subobject and where each column represents a particular feature.

At 212, multiparametric feature data is classified into one or more groups. The subobjects may be groups in accordance with a single feature (e.g., roundness) or multiple features (e.g., roundness, density and area) and classified. The classification may be made based on one (or more) of the following methods:

---

Supervised learning

AODE
Artificial neural network
Back propagation
Bayesian statistics
Naive Bayes classifier
Bayesian network
Bayesian knowledge base
Case-based reasoning
Decision trees
Inductive logic programming
Gaussian process regression
Gene expression programming
Group method of data handling (GMDH)
Learning Automata
Learning Vector Quantization
Logistic Model Tree
Minimum message length (decision trees, decision graphs, etc.)
Lazy learning
Instance-based learning
Nearest Neighbor Algorithm
Analogical modeling
Probably approximately correct learning (PAC) learning
Ripple down rules, a knowledge acquisition methodology
Symbolic machine learning algorithms
Subsymbolic machine learning algorithms
Support vector machines
Random Forests
Ensembles of classifiers
Bootstrap aggregating (bagging)
Boosting (meta-algorithm)
Ordinal classification
Regression analysis
Information fuzzy networks (IFN)
Restricted Boltzmann Machine
Conditional Random Field

---

Statistical classification

ANOVA
Linear classifiers
Fisher's linear discriminant
Logistic regression
Naive Bayes classifier
Perceptron
Support vector machines
Quadratic classifiers
k-nearest neighbor
Boosting
Decision trees
C4.5
Random forests
Bayesian networks
Hidden Markov models
Association rule learning Apriori algorithm
Eclat algorithm
FP-growth algorithm
Unsupervised learning Artificial neural network
Data clustering
Expectation-maximization algorithm
Self-organizing map
Radial basis function network
Vector Quantization
Generative topographic map
Information bottleneck method
IBSEAD
Hierarchical clustering Single-linkage clustering
Conceptual clustering
Partitional clustering K-means algorithm
Fuzzy clustering
Reinforcement learning Temporal difference learning
Q-learning
Learning Automata
Monte Carlo Method
SARSA
Others Data Pre-processing
Feature data types:
Jenk's Natural Breaks

---

The result of the operation at 212 is a definition of at least one group of objects having the feature(s) associated with the group.

At 214, the group(s) are displayed. For example, with reference to FIG. 3C and FIG. 3F, a visualization is presented that codes cells within a particular group by, e.g., color. In the visualization, colored squares are provided where each square represents, e.g., a few hundred cells. The visualization graphically presents area of the data that is of interest. For example, areas in blue may be areas where a tumor exits. Thus, the visualization is a heat map showing a display of where the particular classifications defined at 212 exist. The heat map in the example of FIGS. 3C and 3F show that features in green and read are more heterogeneous in the resistant sample, whereas the features are more homogenous in the sensitive sample.

In accordance with aspects of the disclosure, areas in the visualization can be queried to obtain more information. A user may request to be shown areas having round objects. The user may further drill down and request small round objects having only certain dimensions. Thus, a user can zoom in on, e.g., a gland to see if a neighboring gland is classified differently.

Figure 4:
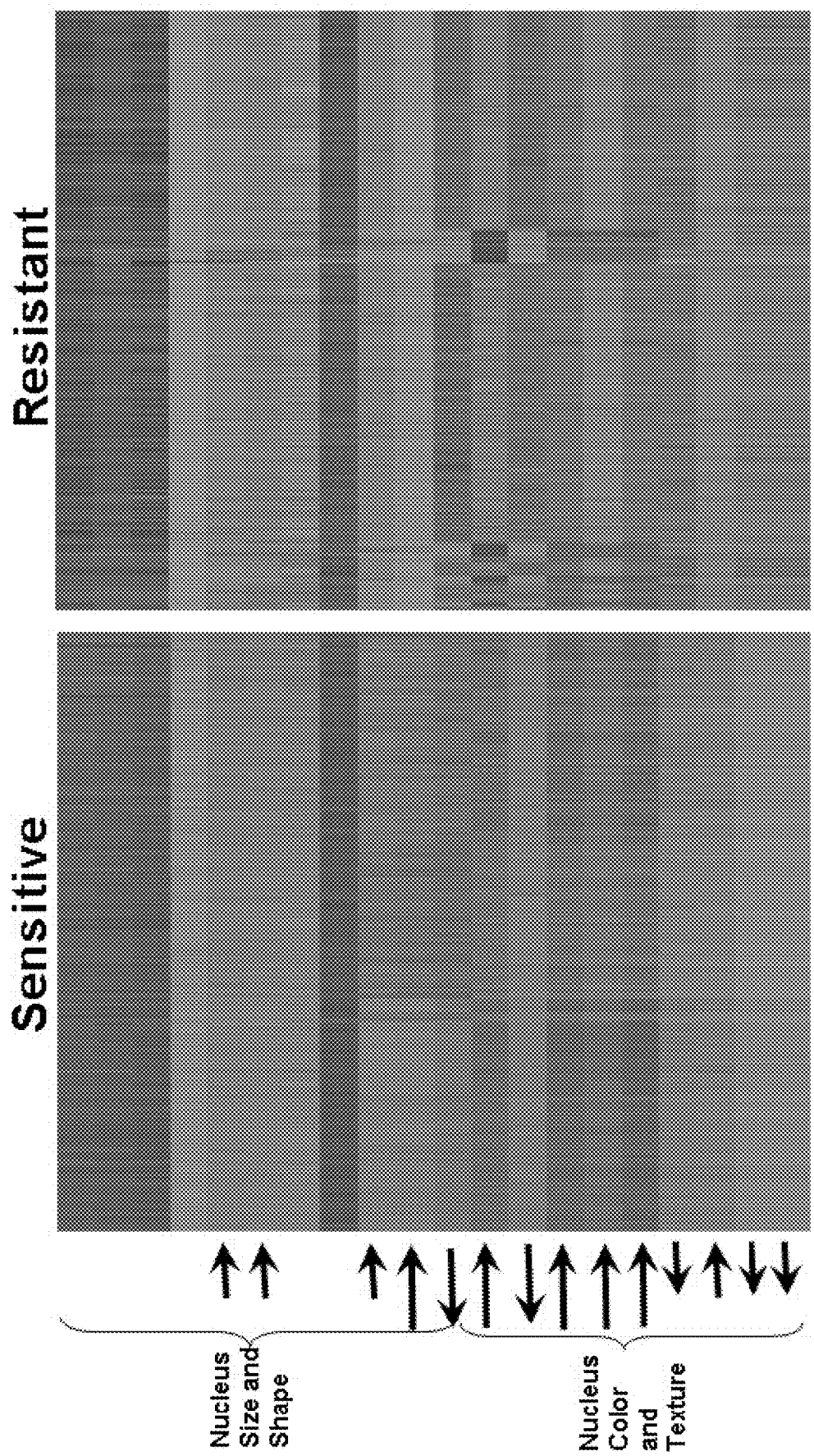

At 216, subobject data may be displayed by feature. For example, FIG. 4 shows the nuclei having particular features. In FIG. 4, the data is organized such that cells are represented in columns and features are represented in rows. Displaying subobject data enables delineation of groups based on clinical applications, such as clinical resistance, short survival, etc. Accordingly, if a pathologist knows there is cancer, the feature data can be used to predict how cancer will perform.

Thus, the above operational flow presents a method by which feature data can be classified and displayed visually.

Tumor Complexity and Micro-Environmental Analysis within Digital Image Analysis

The present disclosure also provides methods and system for investigating evolutionary and ecological forces that govern heterogeneity in, e.g., breast cancers. Recent studies have demonstrated substantial genetic heterogeneity in cells within the same tumor as a result of intratumoral evolution. Generally, this heterogeneity is viewed as a genetic process in which stochastic mutations generate new populations in an unpredictable if not chaotic process. However, genetic changes are one component of evolution and that intratumoral Darwinian dynamics emerge fundamentally from environmental selection forces that promote phenotypic (not genotypic) adaptations.

The present disclosure is based on a principal that intratumoral cellular variation represents a predictable process driven by variations in environmental selection forces leading to predictable and reproducible adaptive strategies. The most obvious source of environmental selection is tumor complexity which, in most cancers, is spatially and temporally variable resulting in (but not limited to) regions of poorly perfused tissue, collagen rearrangement, hormonal and inflammatory response. Each of which the spatial variability is evaluated.

As with any common phenotypic trait, it is assumed that variability will be observed only if it provides an adaptive advantage. Specifically, trait changes will be expressed only when variation is present in the microenvironment. When vasculature is absent an expenditure of resources and will be selected against. Different morphotypes of cells will be found in regions of high blood flow compared to regions of poor blood flow. This results in the prediction that the prevalence of certain cell types will generally follow the distribution of resources in the microenvironment. Furthermore, diversification of cell types leads to increased probabilities that some cells will survive given inevitable resource changes in the dynamic environment, including cancer treatments.

It is generally accepted that genetic heterogeneity among cancer cells is a manifestation of intratumoral evolution, and this is typically viewed as a consequence of random mutations generated by genomic instability within the cancer cells. However, this represents an incomplete view of Darwinian dynamics, which typically are governed by phenotypic variations in response to spatial and temporal variation in environmental selection forces. In accordance with implementations herein, pathologic feature analysis can provide precise information regarding regional changes in environmental selection forces and phenotypic adaptations. These observations can be integrated using quantitative, spatially-explicit methods developed in ecology to define the underlying variability in biological processes in tumors and their microenvironment within individual patients.

Heterogeneity between cancer cells has long been recognized as a property of cancer progression and resistance to therapeutic intervention. Somatic evolution in the progression of cancer is often investigated through genetic heterogeneity and measured in terms of single nucleotide polymorphisms, sequence mutations, and chromosomal abnormalities. While genetics and signaling networks are the basis of core traits; the adaptive evolution and even diversification of cell traits in response to the diverse conditions within the physical microenvironment (PME) may dictate trends in tumor growth dynamics.

The evolution of breast cancer can be probed by evaluating multiparametric morphological features of single cells of tumors and the microenvironment in histology sections in accordance with the disclosure herein. The proposed multidisciplinary approach of joining intratumoral and microenvironmental complexity measures to shed new light on cancer research. Tumor tissue is composed of a myriad of cells that can differ in multiple core phenotypic traits and thus respond to changes in the host environment in different ways. This intratumoral cell heterogeneity may carry valuable information about the tumor's ability to take advantage of adaptive opportunities but is not always possible to identify with single visual features.

Tumor rugosity is, thus, a useful metric for elucidating tumor complexity which in turn will inform investigators about the relationship between the tumor and its local PME and its ability to adapt to changing environments.

Figure 5:
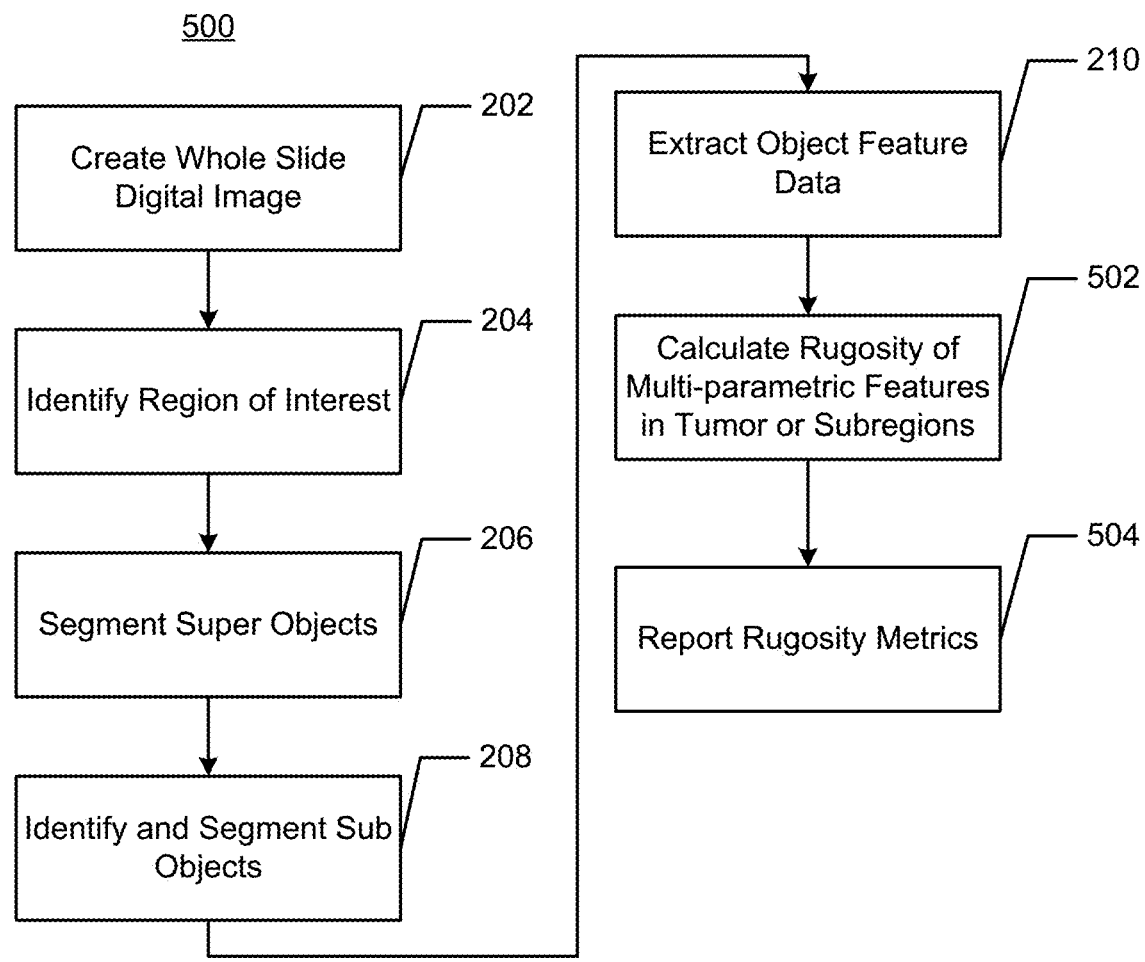
FIG. 5 illustrates another example operational flow wherein a rugosity of multiparametric features is determined.
Figure 6:
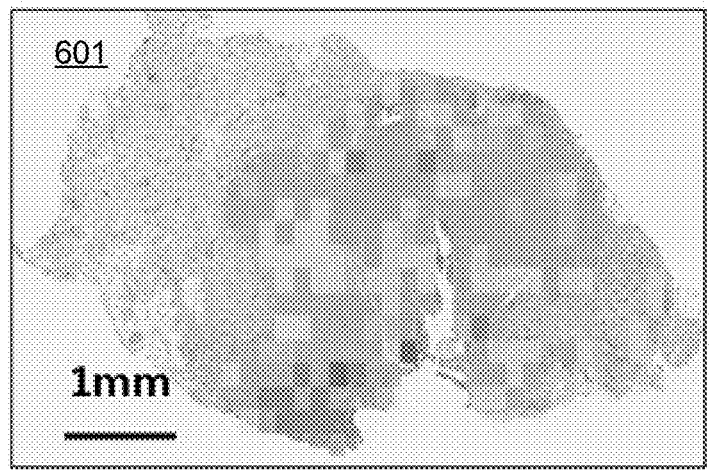
FIG. 6 illustrates an output of the operational flow of FIG. 5.

The relationship between invasion rate and tumor heterogeneity may be a key to cancer control. FIGS. 5 and 6 demonstrate methods for evaluating the rugosity of the feature data set described above for spatially localized subpopulations of cells with rugosity of individual features and features in combinations with other traits, using data classification techniques (such as cluster or discriminant analysis) and correlating these results with their spatial location. Correlating quantifiable tumor cell features to trait evolution within an adaptive landscape may yield insight into cancer cell fitness, their ability to adapt to fill niches when the opportunity arises within an adaptive landscape and novel methods to understanding tumor cell invasion.

FIG. 5 illustrates an operational flow diagram 500 in accordance with another aspect of the present disclosure wherein rugosity of multiparametric features is determined. In FIG. 5, operations performed at 202-210 are the same as discussed above with regard to FIG. 2. As such, the operations at 202-210 will not be repeated again. At 502, a rugosity of multiparametric features of a tumor or within subregions is determined. As noted above, diverse cell populations are indicative of resistant cancer populations. The rugosity is a measure complexity/diversity/variation within a tissue region and may be calculated as a single metric as follows:

$$fr = Ar/Ag,$$

where $fr$ is the rugosity;
$Ar$ is the surface area; and
$Ag$ is the geometric surface area.

At 504, a report of the rugosity metrics is made. This may be a visualization 601, as shown in FIG. 6, where the rugosity metric value is shown by variations in color. As shown, a user may apply a checkerboard over a small population in, e.g., a gland. Populations within the gland can be determined by viewing the green, orange or red regions. An end user can visually inspect how broken up the populations are, how large the population sections are, how homogeneous the populations are, etc.

Microenvironmental Analytics

As noted above, intratumoral cellular heterogeneity represents a predictable process driven by variations in environmental selection forces leading to predictable and reproducible adaptive strategies. The most obvious source of environmental selection is blood flow which, in most cancers, is spatially and temporally heterogeneous resulting in regions of necrosis in poorly perfused regions.

As with any common phenotypic trait, ER expression will be observed only if it provides an adaptive advantage. Specifically, ER will be expressed only when estrogen is present in the microenvironment. When estrogen is absent, ER expression represents a needless expenditure of resources and will be selected against. Since the source of estrogen in the breast is typically (although not always) serum and moves from the vessels into the cell by a simple reaction diffusion model identical to oxygen, nutrients, etc., ER+ cells will be found in regions of high blood flow while ER− cells will be present in regions of poor blood flow. This results in the prediction that the prevalence of ER+ cells will generally follow the distribution of blood flow.

Accordingly, H&E stained histological sections can be used to identify blood vessels using histological pattern recognition or manual identification. The lumen area ($\mu m^2$), vessel perimeter ($\mu m$), distribution of vessel size, spatial density, distance from vessel to nearest vessel, and potentially other vascular related metrics may be used to quantify aspects of vascularity. This multiparametric data set can be used to compare the tumors from different patients with distinctly different ER status. Understanding how overall vascular status affects ER switching is used for in proangiogenic or antiangiogenic therapy decision making.

Figure 7:
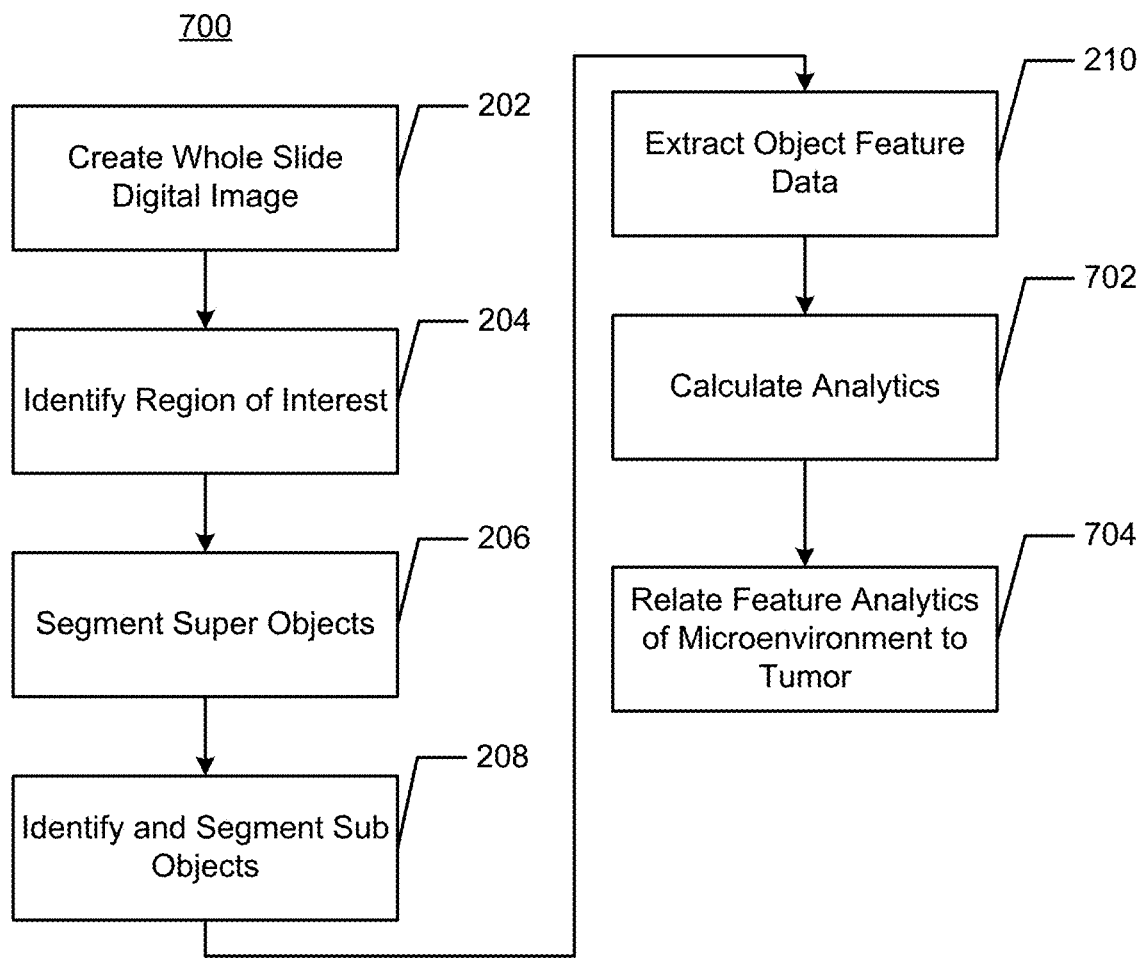
FIG. 7 illustrates another example operational flow wherein evolutionary and ecological forces that govern heterogeneity of ER expression cancers are established through analytics.
Figure 8:
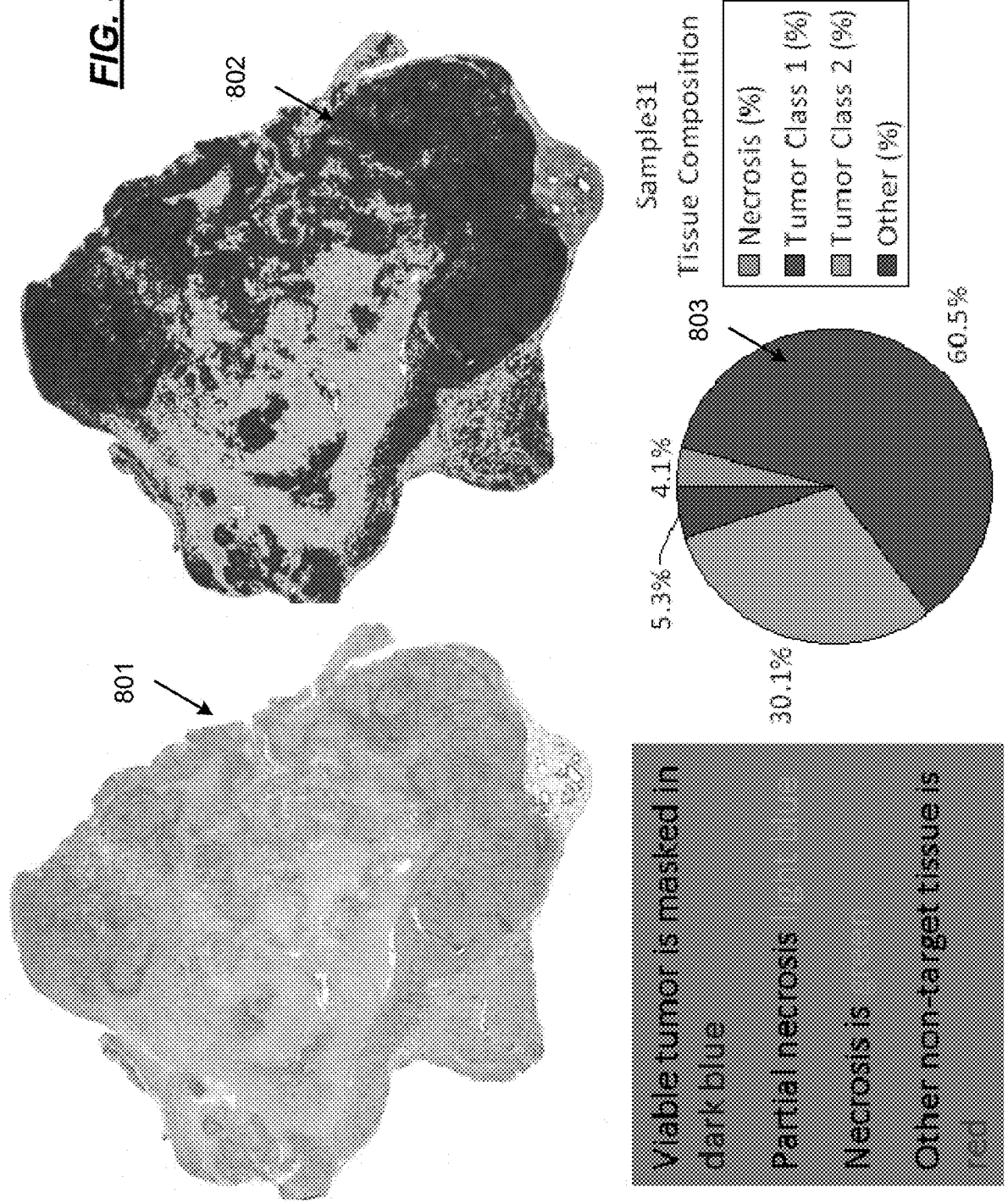
FIG. 8 illustrates an output of the operational flow of FIG. 7.

FIG. 7 illustrates an operational flow diagram 700 in accordance with another aspect of the present disclosure wherein evolutionary and ecological forces that govern heterogeneity of ER expression cancers. In FIG. 7, operations performed at 202-210 are the same as discussed above with regard to FIG. 2. As such, the operations at 202-210 will not be repeated again. At 702, analytics are calculated on the multiparametric data. The analytics derive and measure environmental factors of interest that lead to tumor growth. Such analytics quantify the microenvironment. At 704, the analytics are presented in, e.g., a visualization. FIG. 8 illustrates an example visualization, which shows features of the microenvironment 801, such as tissue composition 802 and a pie chart 803 showing the relative contributions within the tissue composition 802.

Spatial Region Identification within Digital Image Analysis

Overview

Microscopic images of tumor tissue represent a rich source of (underutilized) biological information. Advanced microscopy techniques and image analysis allow for a detailed quantitative assessment of cancer cells' spatial relationship with each other, with normal cells, and with the tumor microenvironment, as well as metabolic state of all cells, all of which can be related to key hallmarks of cancer. These objective, quantitative methods to characterize tumor tissue heterogeneity take into account both morphological and molecular features of tumor and stromal cells. The present disclosure differs from previous image analysis methods in cancer morphometry in at least the following non-limiting aspects. First, in contrast to other approaches, the methods herein are not limited to a predefined set of morphometric features selected by a pathologist. Rather, an extensive quantitative set of cellular features and molecular measurements from the cancer epithelium and the stroma are used. Second, the whole tumor tissue and the surrounding stroma after tumor resection are taken into account together with a panel of several molecular biomarkers. This allows an analysis of the morphological and metabolic state of the whole tumor. Third, static information from pathology samples is combined with dynamical 2D/3D computer simulations using specially designed suite of mathematical models parameterized with individual patient data. This allows the testing of multiple combinations of parameters in a systematic way, and the identification of combinations of microenvironmental factors (such as cell metabolic status, cell-cell and cell-stroma interactions) that are crucial for progression of this specific tumor. That in turn, may provide to novel criteria for both image analysis of tumor histology and for predicting clinical outcomes in individual patients. Fourth, a novel quantitative tool is provided to correlate the likelihood of patient progression free survival with the characteristics of the resected tumor tissue, enhanced by dynamic progression simulations. This may augment the currently used pathologist gold standard that is based on visual inspection of pathology specimens by a trained clinician.

Histology pattern recognition utilizes complex computer learning models which are trained by, e.g., a pathologist. By teaching the algorithm to recognize the same regions described above, a computer can reliably identify the regions of interest in a robust and repeatable way. Individual physical or molecular features derived from the images can be used to catalog populations and relationships between cells or regions and establish testable hypotheses to further interrogate processes of the system. This also creates and thus defines a border between tissue regions. Qualitatively, the regions of interest could then be evaluated. With these tools precise metrics of the regions can be quantified. Initially these metrics might include area, intensity, roundness and other physical features. These regional tissue features can also be quantitatively measured and used to evaluate the disease at a regional scale. Once distinctive environmental regions are identified, the morphological or phenotypic properties of individual cells within that region can be evaluated. In turn, this enables the intratumoral variation to be characterized, quantified and ultimately compared. As will be described below, the present disclosure provides a method for, e.g., pathologists to define the dynamics within cancers through application of methods of quantitative identification and classification analysis of tumor histology. Spatial variation in these tissues can be measured and used to define both prognosis and optimal therapeutic strategies.

Figure 9:
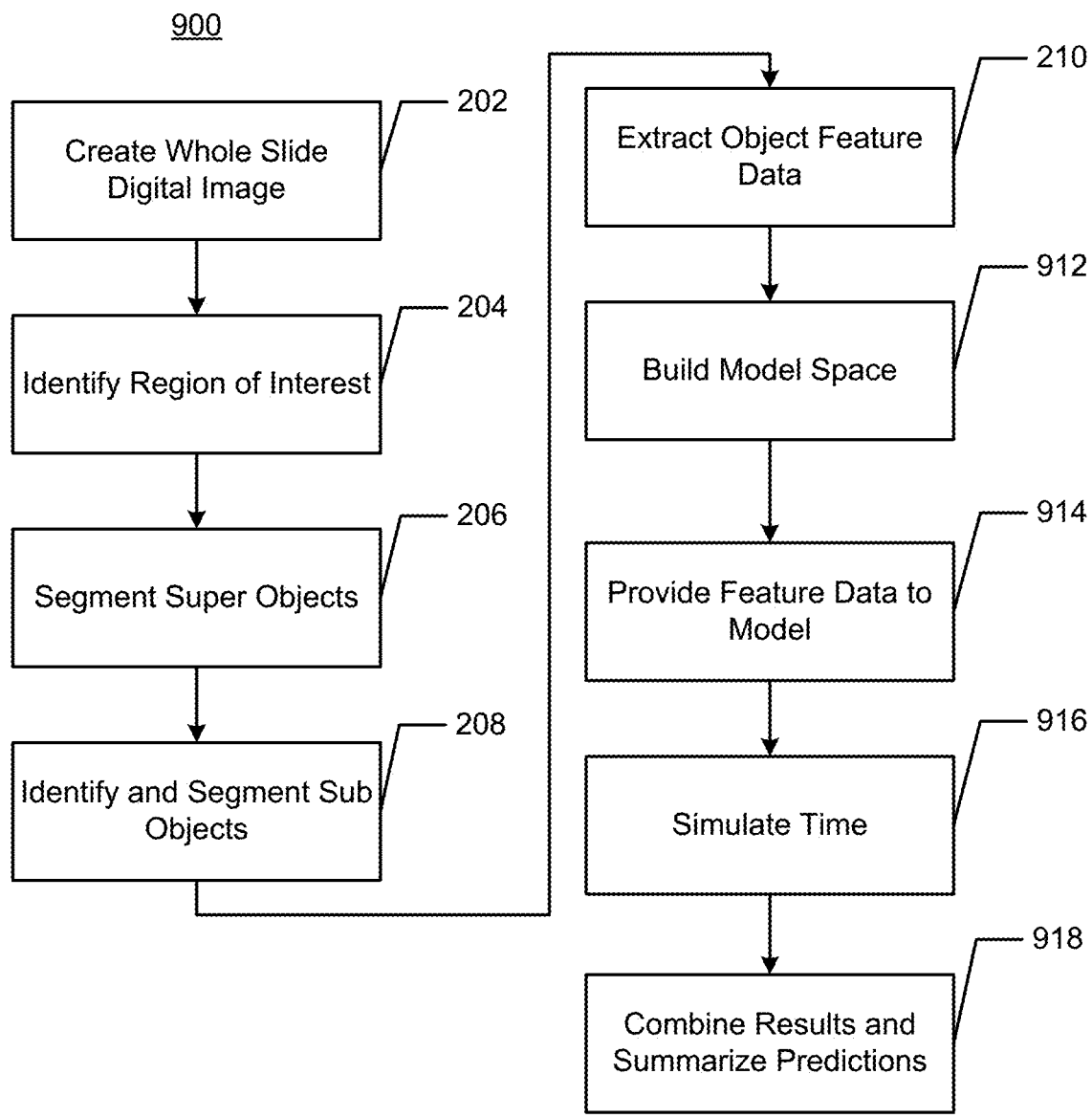
FIG. 9 illustrates an example operational flow.

FIG. 9 illustrates an example operational flow 900 in accordance with present disclosure wherein visualizations of features of digital images are generated from image data. As will be described below, using digitized slides, cell feature data may be identified and displayed to provide a visualization of certain characteristics of tumor cells. In the operational flow 900, steps 202-210 are the same as described above and will not be repeated herein below.

At 912, a model space is built with the object (cell) coordinates. The coordinates may be used to reconstruct a virtualized or digitized tissue. At 914, each object is parameterized into a mathematical model. For example, parameter ranges may be input, such as all nuclei are between x and y $\mu m$, where x and y are predefined. Each term in the model is responsible for simulating aspects, such as how rapidly a cell may grow, how fast a cell may move, etc.

At 916, the models are used to demonstrate how the objects will act over time. For example, the models are run a predetermined number of time steps to determine how the cells will interact over time.

At 918, the results of the models are used to predict how the tissue will respond over time. Thus, the operational flow begins with a digitized sample of tissue, and from the digitized sample, determines how the tissue will act over time in the future by modeling the interactions between the tissue cells or the tissue cells and the environment. Specific implementations of the operational flow 900 are described below with reference to FIGS. 10-15.

Figure 10:
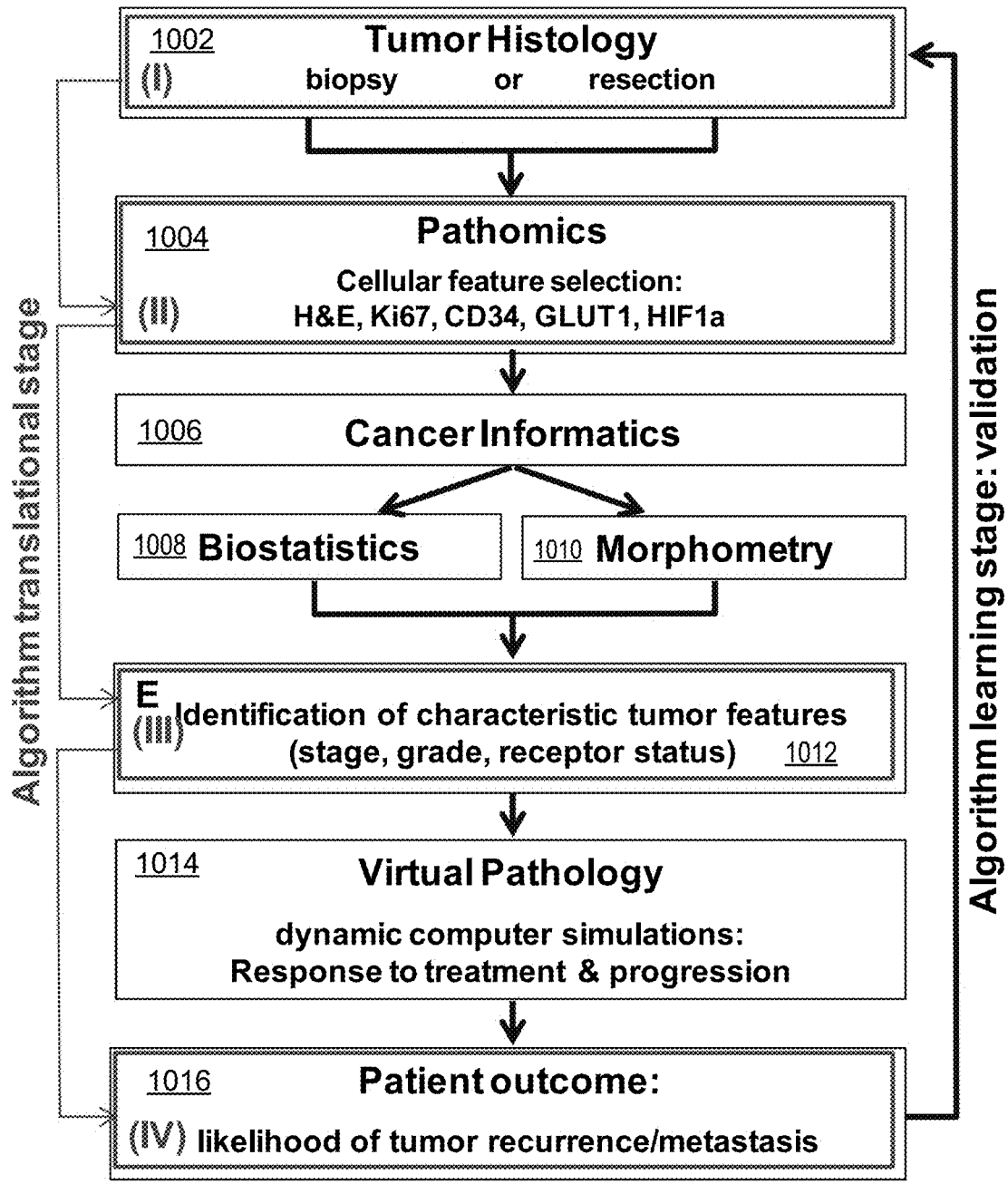
FIG. 10 illustrates an example interdisciplinary design work flow.

In accordance with the present disclosure, an interdisciplinary design is summarized in FIG. 10, which combines a pathologist's review of tumor tissue histology samples (1002), followed by image-based Pathomics analysis of individual cellular features (1004). That may include high-resolution slide scanning, advanced image analysis via customized algorithms for identification and quantification of various cellular and microenvironmental features.

The data that is created is stored in a designated database (1006), and subjected to both multidimensional statistical and morphometrical analysis (1008 and 1010) to identify quantitative features of individual cells that are characteristic for a given tumor type, grade, stage or hormonal status (1012). These cellular features divided into similarity classes are used to determine combinations of cellular traits (phenotypes) for Virtual Pathology models parameterization. Moreover, the computational models take advantage of patient-specific histology to decide on localization of tumor vasculature as a source of nutrients and chemotherapeutic agents, localization of proliferating cells and regions of tumor hypoxia (e.g., identified by Pathomics via adequate staining: CD34, Ki67, HIF1a, respectively at 1002). Subsequently, the models are used for simulations of tumor progression under various combinations of parameters representing different tumor cell responses to environmental cues and treatments (1014). The outcomes are finally correlated with patient progression free survival (PFS) status (1016).

It is typical for mathematical models to be developed in two stages: in the learning stage model outcomes are compared to known patient's outcome to validate the models; in the translational stage the models are used to predict potential outcomes for various treatment scenarios in order to assist in choosing the optimal treatment. Both modules, Pathomics and Virtual Pathology, are independent, but inform one another, as the quantitative features from Pathomics can be used for Virtual Pathology model parameterization, and the outcomes from the latter can be used for specifying new criteria for image analysis. This approach leads to (1) development of objective, quantitative metrics to characterize tumor heterogeneity based on quantitative image analysis techniques that correlate with patient progression outcome; to (2) predictions of subsequent tumor behaviors, including recurrence or metastases by simulating mathematical models that explicitly include the complex tumor-host dynamics; (3) to specify new criteria for image analysis of histology samples.

With reference to FIGS. 11A-11E, 2D/3D Virtual Pathology computational models for simulating tumor progression in response to treatment have been developed based on previous experience in building mechanistic models of individual tumor cells and tumor cells interactions with the microenvironment. In these suite of modeling frameworks, tumor and stromal cells are represented as individual entities that can interact with one another and with their immediate environment, which is represented by the extracellular matrix fibril structure and/or by dissolved gradients of metabolites. Below are example modeling frameworks that demonstrate the above.

$$\rho\left(\frac{\partial u(x,t)}{\partial t} + (u(x,t)\cdot\nabla)u(x,t)\right) =$$
$$-\nabla p(x,t) + \mu\Delta u(x,t) + \frac{\mu}{3\rho}\nabla s(x,t) + f(x,t),$$

$$\rho\nabla\cdot u(x,t) = s(x,t),$$

$$f(x,t) = \int_\Gamma F(l,t)\delta(x-X(l,t))dl,$$

$$s(x,t) = \sum_{k\in\Xi^+} S_+(Y_k,t)\delta(x-Y_k) + \sum_{k\in\Xi^-} S_-(Z_m,t)\delta(x-Z_m),$$

$$\frac{\partial X(l,t)}{\partial t} = u(X(l,t),t) = \int_\Omega u(x,t)\delta(x-X(l,t))dx,$$

$$\frac{\partial \gamma(X(l,t))}{\partial t} = \kappa_1(X(l,t)) - \kappa_2\gamma(X(l,t)).$$

An Immersed Boundary Model $$F_i^{tum} = \sum_{j\in N_i^{tum}} F_{ij} + \sum_{k\in N_i^{opi}} F_{ik} + \sum_{l\in N_i^{myo}} F_{il} + \sum_{m\in N_i^{bmemb}} F_{im}$$

$$F_{ij}(t_n) = \mu_{tum}(|r_i(t_n) - r_j(t_n)| - L_{tum})\frac{r_i(t_n) - r_j(t_n)}{|r_i(t_n) - r_j(t_n)|}$$

$$r_i(t_{n+1}) = r_i(t_n) + F_i^{tum}(t_n)\frac{\Delta t}{\eta}$$

A Particle-Spring Model

Figure 11A:
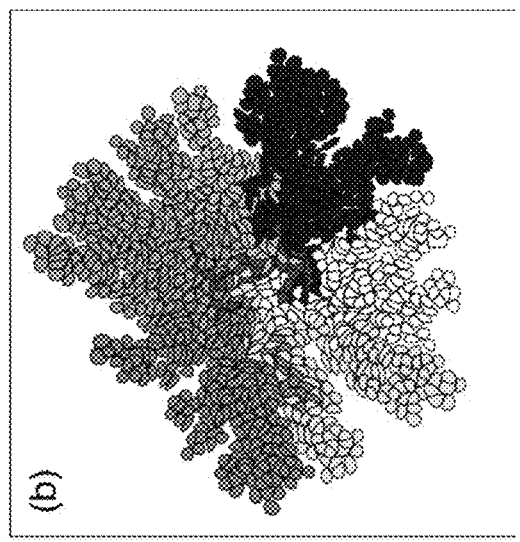
FIGS. 11A-11E illustrate visualizations related to an application of 2D/3D virtual pathology computational models for simulating tumor progression in response to treatment.
Figure 11B:
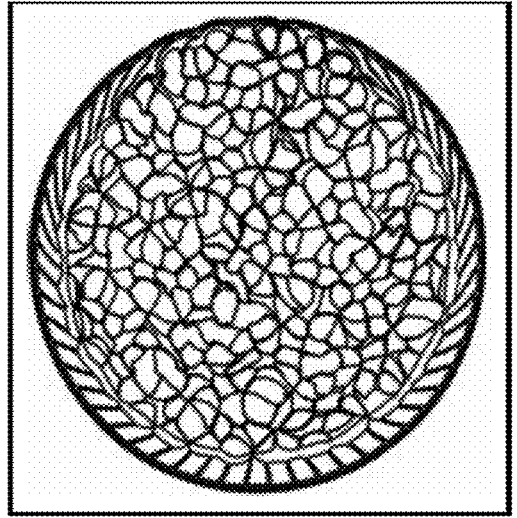
Figure 11E:
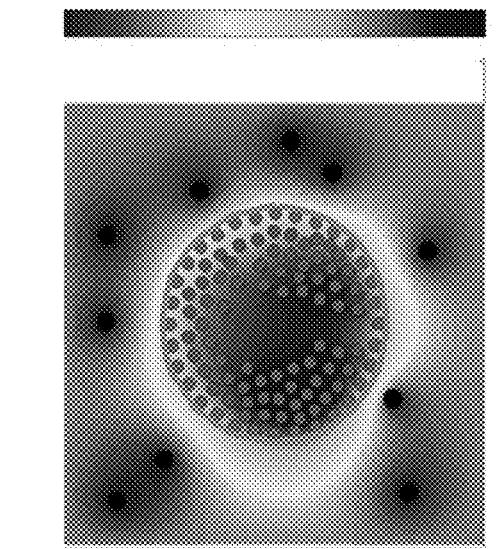
Figure 11D:
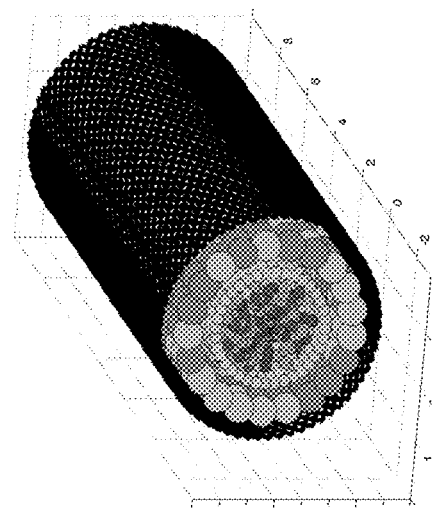
Figure 11C:
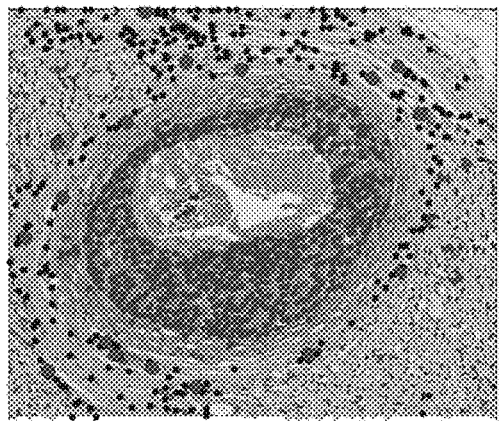

FIGS. 11A-11B show the immersed boundary fluid-structure interactions model of individual deformable tumor cells grown inside the duct (FIG. 11A) or as a multiclonal colony (FIG. 11C). FIGS. 11C-11E show particle-spring model of 2D section through DCIS and tumor stroma (FIG. 11C), the 3D DCIS structure (FIG. 11D), and the 2D DCIS with oxygen distribution from the surrounding vessels (FIG. 11E). A feature of the above models is their initiation with tumor and stromal cell configurations extracted from microscopy images, which is directly shown in FIG. 11C by overlying the histology and computational images. The distributions of various tumor metabolites are determined by Pathomics. Each cell is equipped with a phenotype, that is a set of cell properties that determine how the cell initiate its life processes and how it responds to microenvironmental cues. The phenotype of each cell is determined using cellular features quantified from the H&E or IHC images via Pathomics by associating them with specific computational attributes, as show in Table 1 below.

TABLE 1

Example of cellular and microenvironmental features extracted from microscopy images (Physical and Molecular features), and quality input to the IBCell model (Computational traits)

| Physical | Computational Tumor regions | Molecular features | Computational | Physical Microenvironment | Computational feature |
|---|---|---|---|---|---|
| Cell size | Cell size | HIF-1 | Low oxygen gradient | Fibrotic location | ECM structure |
| Cell-cell distance | Cell-cell distance | CA 8 | Hypoxia level | Vessel localization CD34 | Source of nutrients |
| Cell roundness | Quiescent vs. mobile | GLUT-1 | Metabolic state of a cell | Vessel size/lumen area | Functional vasculature |
| Nuclear size | Cell proliferation/ death | MMP-7 | Cell adhesion | Inflammatory cell localization | Stromal cells |
| Nuc condensation | Cell proliferation/ death | E-cadherin | Cell adhesion | Inflammatory response IL8 | Tumor-stromal cells |
|  |  | Ki67 | Proliferating cell |  | Interactions |

Additional cellular features can be developed as needed. Some of the cellular features can be associated with multiple cell actions (i.e., increased nuclear condensation can be a symptom of either cell proliferation or cell apoptotic death). In these cases multiple simulations are run to examine whether changes in behavior of individual cells have impact on the overall tumor morphology and tumor metabolic status. Moreover, various interactions between tumor cells, as well as between tumor cells and their microenvironment are examined by systematically changing specific threshold values (i.e., thresholds for metabolic compounds sensed by the cells from their vicinity upon which the cells enter into a particular cell life process: proliferation, death, contact inhibition, ECM adhesion). This systematical search of threshold values allows for simulating various scenarios of tumor progression, and pinpoint the cellular features and microenvironmental factors that either promote or prevent tumor advancement.

Figure 12:
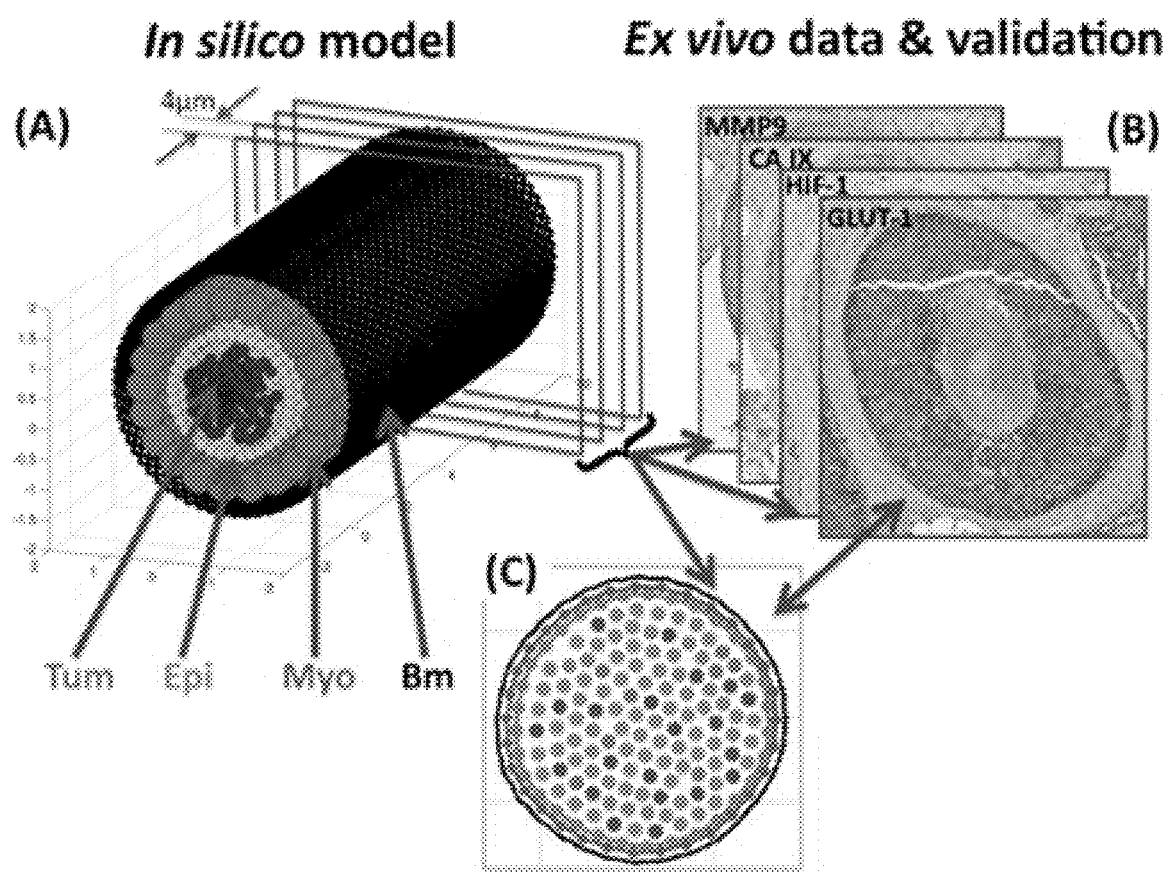
FIG. 12 illustrates a computational reconstruction of tumor tissue.

With reference to FIG. 12, there is illustrated a computational reconstruction of tumor tissue. In the case of the 3D models, the consecutive tissue slices (z-stack) are used to reproduce tumor tissue architecture and its full metabolic landscape. Tissue slices are typically cut at 4 μm width that enables co-registration of all tumor cells across 3-4 consecutive slices and reconstruction of cell three-dimensional locations. Also, typically, each tissue slice is stained using a different IHC biomarker and advanced computational reconstruction techniques are used to extrapolate biomarker values from the one stained slice to two neighboring slices.

Figure 13:
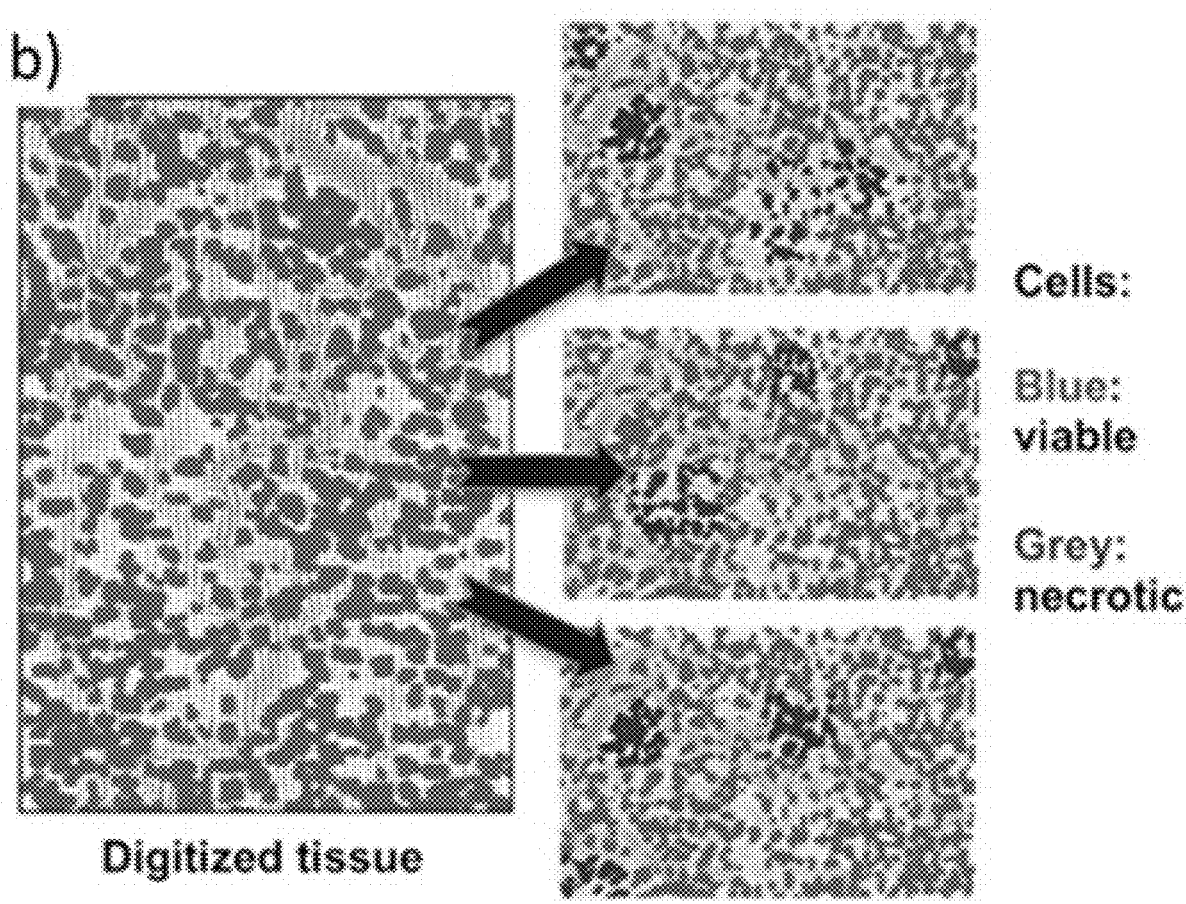
FIG. 13 illustrates example results from a series of virtual pathology simulations.

With reference to FIG. 13, there are illustrated typical results from a series of Virtual Pathology simulations. Starting from the same initial tissue configuration model outcomes are obtained by modifying model parameters, and three typical outcomes of Virtual Pathology simulations are shown. In accordance with the present disclosure, model predictions are generated by performing high throughput simulation studies in which multiple parameters are varied simultaneously over a wide range of model parameters. Starting from the same initial model state (for example, the same tumor tissue structure and metabolic landscape), final model outcomes are produced that can forecast tumor behavior under a treatment defined by model parameters. Model outcomes obtained by systematically modified parameters are then collected and grouped into similarity classes. The resulting multidimensional parameter space is then inspected to identify combinations and ranges of key model parameters (and the underlying cellular or microenvironmental features) that result in tumor optimal response. In this way we can establish conditions (in many cases expressing non-linear relationships between their components) under which a given tumor will progress or not. These conditions will point to metabolic or signaling mechanisms that were previously not considered. This can be used in two ways. First, novel criteria for the analysis by the Pathomics module can be defined. Second, the optimal treatment strategies determined by computer simulations can inform further laboratory experiments. The goal of this tool is, in part, to interrogate cell phenotypic heterogeneity in a given microenvironment, and to establish correlations between outcomes simulated based on patient histology data and patient survival.

Figure 14:
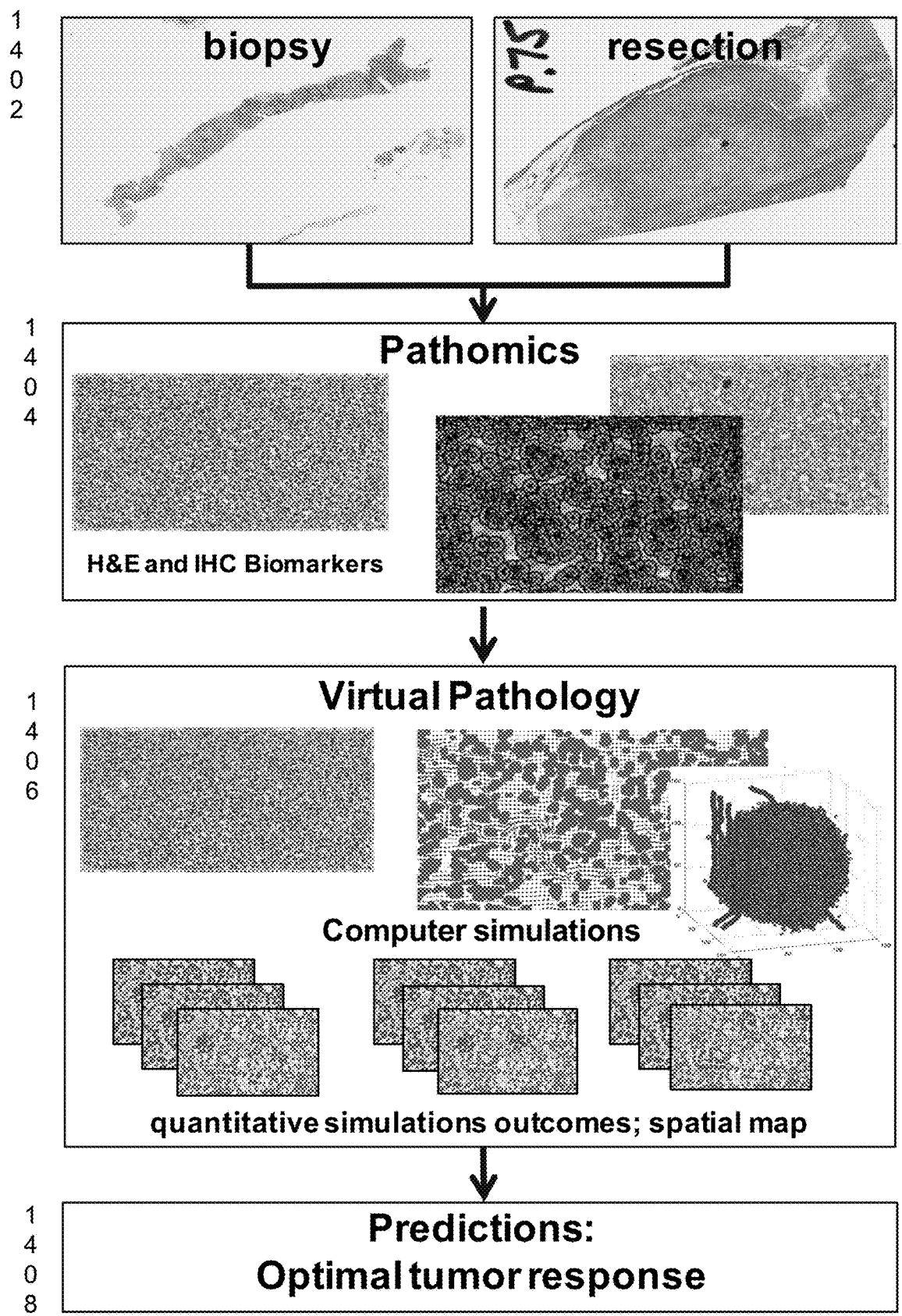
FIG. 14 illustrates an example pathomics/virtual pathology simulation procedure.

FIG. 14 illustrates an example Pathomic/Virtual Pathology simulation procedure. The simulation procedure consists of using the model parameterization with patient-specific tumor morphology (1402), including localization of tumor vasculature, localization of proliferating cells and regions of tumor hypoxia and tumor cells glycolytic state assessed from immunohistochemistry staining, as well as individual cellular features that characterize each type of tumor and identified by Pathomics (1404). The vasculature may act as a source of therapeutic agents and nutrients; Ki67 staining will determine the tumor proliferative index and define the initial population of proliferating cells; HIF1a and GLUT1 will define the initial metabolic state of tumor cells. An extensive series of simulations is run for each patient tissue. By systematically varying parameters defining cell doubling time, metabolic state and sensitivity to therapeutic compounds the models can produce multi-parameter report charts of tumor response to a typical treatment schedule. The analysis of all simulation outcomes (three potential outcomes are shown in 1406), such as the extent of specific resistant cell subpopulations, as well as spatial localization of viable cells within the tissue metabolic and vascular topography (relative localization of vasculature and tumor cells, as well as tumor cell metabolic status), can determine the likelihood of a patient tumor recurrence (calculated as a percentage of computer simulations classified as recurrent). In this class of survival models tumor and stromal cell's morphometric parameters and expression levels of molecular biomarkers may be taken into account to provide a prediction of optimal tumor response (1408).

In summary, the present disclosure describes a verified protocol for determining a minimal set of cellular and environmental features quantified from histological images that characterize tumor heterogeneity and correlate with patient survival outcome to interrogate tumor progression. The computational models described here can be applied as high-throughput automatic analysis of large numbers of diverse tumor cases. The described quantitative and dynamic tool can be incorporated into the pathologist's diagnostic toolbox to assist in the evaluation process cancer progression likelihood, and to help inform therapy decisions. The above examples are presented for illustrative purposes and do not limit of the present disclosure, as other computational models and procedures may be used.

Landscape Pathology within Digital Image Analysis Overview

Detailed molecular data from multiple regions in the same tumor has demonstrated striking variations so that many populations with different biomarkers and gene signatures can co-exist. This indicates an increased need for greater understanding of tumor heterogeneity at molecular, cellular, and tissue temporal and spatial scales. Pathology can be extended to identify, classify and quantify these heterogeneities to supplement the current efforts of personalized medicine. For example, topographical analysis of histological samples within a spatial context may be investigated by employing the theories, tools and experience of landscape ecology.

Variation, and in particular spatial heterogeneity of physical features, is principally studied in the discipline of landscape ecology. Since the pioneering work of Carl Troll in 1939 landscape ecologists have focused on the interactions of populations of organisms and their environments, often using observation and quantification of images of various scales. These same principles can be used to develop a proposed approach termed "landscape pathology". Illustrative examples are provided in FIGS. 16A-16G, which are discussed herein below.

The present disclosure provides a method of pathological analysis using landscape topography to identify and evaluate regional feature variability in pathological images. Tumors can be understood by characterizing and embracing their underlying evolutionary dynamics, including both spatial and temporal variability. Identification of cellular heterogeneity should be regionally explicit, quantitative and reproducible and have high throughput.

Landscape ecology and landscape connectivity, supported by computational analysis, can be utilized to inform pathology using a range of available tools and theories to evaluate specifically the relationship between pattern and process. While pathology is equipped to identify the patterns, landscape ecology and connectivity, together with outlier analysis provides the tools to use these patterns and outliers to understand the underlying biological relationships. Together, quantifiable metrics of digital pathology and landscape ecology can contribute to personalized medicine. Thus, "landscape pathology" has the potential to provide new information on the intratumoral evolutionary dynamics in individual patients.

Landscape Pathology

Darwinian interactions of environmental and cellular adaptations can be extracted from digital slides, as well as regional variations of those dynamics. This utilizes landscape ecology, which focuses on the feedback loops between patterns and processes. Four types of spatial structures (patterns) and their utility to pathology are described.

Figure 15:
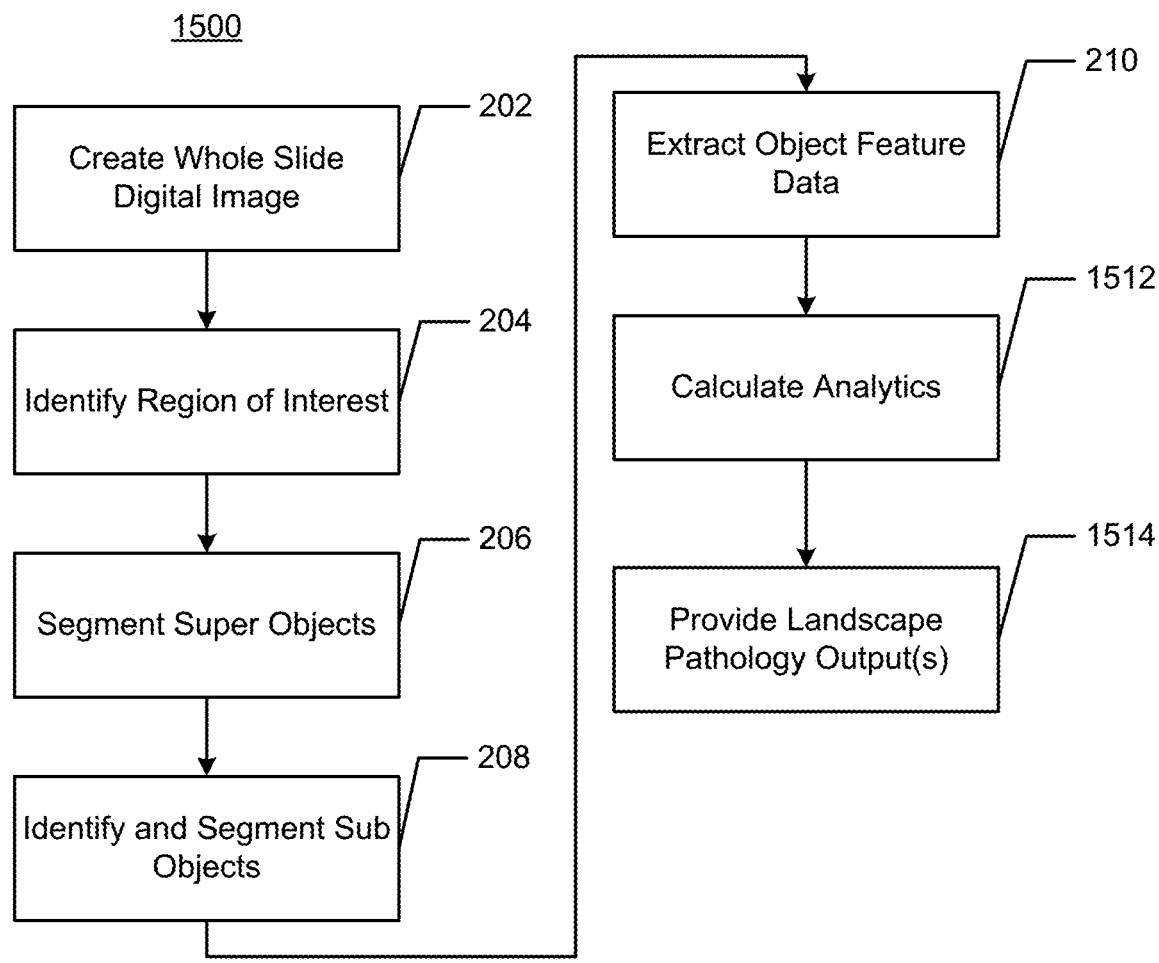
FIG. 15 illustrates an example operational flow to implement landscape pathology.

FIG. 15 illustrates an example operational flow 1500 in accordance with present disclosure wherein visualizations of features of digital images are generated from image data. As will be described below, using digitized slides, cell feature data may be identified and displayed to provide a visualization of certain characteristics of tumor cells. In the operational flow 1500, steps 202-210 are the same as described above and will not be repeated herein below.

At 1512, analytics are calculated on the multi parametric data. The analytics derive and measure environmental factors of interest that lead to tumor growth. Such analytics quantify the microenvironment. At 1514, the analytics are applied to provide the landscape pathology outputs. For example, from the input image shown in FIG. 16A, point patterns may be studied as point locations distributed in two-dimensional space. This is illustrated in FIGS. 16B and 16C. FIG. 16B shows spatial distributions of cells of different sizes, where small cells are in red, medium cells are in green, and large cells are in blue. FIG. 16C shows the same distribution as FIG. 16B with cell size represented by a height of a data point (e.g., a hill-and-valley map). Landscape ecologists would analyze these as normal distribution, random, regular or clustered. In pathology point patterns allow analysis of distribution of some cellular or tissue property (i.e. nuclei) within the tumor in a quantifiable manner. The metrics can be further interpolated to determine the cluttering and distribution of these structures with metrics including the Ripley's K pattern analysis function and can be described as a means to detect spatial heterogeneity.

Figure 16D:
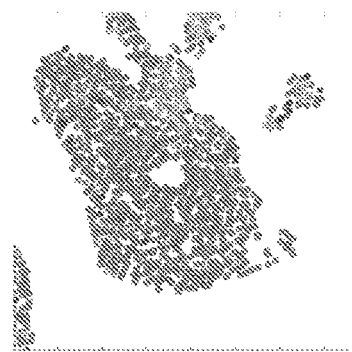

In some implementations, regional variations can be described. For example, continuous or fragmented patterns can be defined and themselves might vary within regions of the tumor. Spatial autocorrelation can, for example, quantify dispersal (migration) of specific cell populations by evaluating nearest neighbors depicted as a correlogram (depiction of correlated statistics in graphical or similar formats) and interrogated with Moran's I equations. This is illustrated in FIG. 16D, which shows clustered patterns. Cells are divided into four similarity classes for two features: cell size and optical density of cell cytoplasm/nucleus, where both low values is in red, both high values is in magenta, size low and optical density high is in green, cell size high and optical density low is in blue. The threshold values separating high form low values for each feature separately were determined using a proposer clustering techniques (such a K-means clustering with rectilinear distance metric). The invasive cohorts have predominantly small cells of high optical density, i.e., the green areas.

Figure 16F:
Figure 16E:
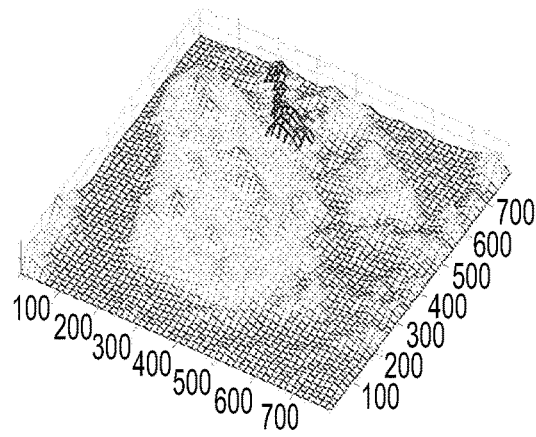

In some implementations, another third pattern to be described is network patterns. In landscape connectivity, inferences about communication or invasion are used for understanding the broader populations and regions. Distance measures and clustering methods are frequently used tools to collect quantitative data. The number of interactions with neighbors in a nearest neighbor analysis, buffered analysis or a spatial autocorrelation to discern morphological or other similarities between nearby individuals can inform the investigator about the size and connectivity of pockets of cells with distinct morphologies. Statistically these subpopulations of individuals with similar physical features can be measured using an abundance weighted index such as the Bray-Curtis index. For example, quantifying distance measures given differences in features is a useful metric for the suggestion of the identification of species. An example analysis of node connections of cell populations with similar features shown is available in FIG. 16E, which illustrates connectivity patterns. FIG. 16E is a hill-and-valley map showing spatial distribution of the values of optical density feature (red-high values, blue-low values) with overexposed a path (black) connecting cells forming an invasive cohort protruding from the DCIS.

Figure 16G:
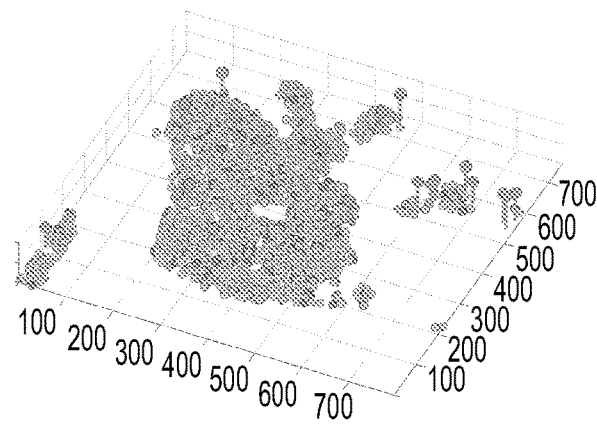

In some implementations, the elements of the landscape that differ from the patterns described above (i.e., the pattern outliers) may be considered. The methods used for analysis of three previous patterns relay on similarities (distributions, correlations, clusters) between pattern components. Also, in standard statistical analysis these elements are usually disregarded as statistically non-significant. However, it is widely accepted that tumors arise from single cells that have accumulated certain mutations giving them proliferative and survival advantage. Thus, such individual tumor precursors constitute outliers among all other surrounding cells, both genetically (their mutations differentiate them from other cells having normal genome) and phenotypical (their proliferation potential is different from other cells). Identification of such outliers can inform the investigator about the untypical cells that may drive tumor progression. This is illustrated in FIGS. 16F and 16G, which show outlier patterns. FIGS. 16F and 16G illustrate both cell size and pixel density are high in the cell indicated by magenta and high vertical pin-lines.

Thus, patterns, processes and predictions give rise to possibilities to build a new paradigm for addressing cancer treatment. As such, pathologists have the opportunity to define the spatially explicit subpopulations of cells within cancers through application of methods and principles of landscape ecology to an analysis of tumor histology. Using automated image analysis techniques, both key environmental selection forces and cellular adaptive strategies can be determined. Furthermore, spatial variation in these tissue "habitats" can be measured and used to define both prognosis and optimal therapeutic strategies. The latter will require transition from targeted therapies based on genomic analysis of small tumor samples to environmentally- and phenotypically-defined targets based on comprehensive knowledge of the spatial variations throughout the tumor. This is possible with automated, high throughput image analysis technologies to identify variations in the physical or molecular metrics of cells and environmental properties within the primary tumor coupled through computational models adopted from ecology.

Pathology Case Review, Analysis and Prediction Overview

The present disclosure describes systems and methods for personalized cancer therapy, using genetic analysis for target lesions in a single sample that averages the genomes of a relatively large number of cells are not optimal. As will be described below, The enormous progress in understanding the molecular basis and pathophysiology of cancer has not generally translated into significantly improved outcomes. The currently used screening methods (such as radiological imaging: FFDM or MRI) and grading criteria take into consideration a limited number of factors when assessing tumor aggressiveness. In fact, histological grading of breast cancer (Nottingham Scoring) has remained unchanged since the 1920's, and only takes into account 3 visually-identifiable criteria and represents only a 6% difference in 5-year progression-free-survival. This is despite massive implications of the various treatment paradigms associated with each grade.

It is clear the current prognostic methods remain relatively subjective, non-quantitative and based on static information (i.e., pathology specimens are taken at the single time point of tumor biopsy). Amazingly, the point of diagnosis, the pathology, is the last remaining analogue medical science. These limitations are addressed here by considering currently used screening systems while developing and testing new screening tools that combine advanced image analysis with computational algorithms for cellular feature classification and mathematical modeling of tumor progression. Sets of measurable imaging features reflecting the underlying molecular characteristics of the tumor cells that can be identified and quantified using image analysis and computational modeling can be available. A systematic and high-throughput analysis of image-based cellular features will allow us to inspect and categorize simultaneously multiple morphological properties of large numbers ($>10^6$) of cells per patient in order to identify subpopulations of phenotypically different tumor cells that have prognostic value in predicting tumor invasiveness.

This allows us to identify predictor cells that form relatively small subpopulations or are spatially scattered, and thus are typically missed by currently used prognostic methods, such as the current histopathological review. This in turn, will enhance tumor screening and its evaluation.

The multidisciplinary expertise including pathologists, digital pathology image acquisition specialists, image analysts, software designers, database experts, bioinformaticists and biostatisticians may be combined to develop companion diagnostic tools for pathologists. This provides an opportunity to quantify the imaging characteristics tumors of various grades and to relate those mineable data with their local environments (vessel density or inflammatory response). The clinical and pathologic characteristics of the tumor at the time of presentation, and the long-term outcomes for each longitudinally consented patient can be minable data as well.

The present disclosure combines sets of patients' Standard of Care examination results acquired retrospectively from tumor databases and (i) a pathologist's review of tumor tissue samples from core biopsy or excisional tissues followed by (ii) high-resolution whole slide image digitization using slide scanning and advanced image analysis via customized algorithms for identification and quantization of various cellular and microenvironmental features. The obtained multifactor data is then (iii) divided into similarity classes using computational classification methods allowing for determination of small cell subpopulations with phenotypes (combinations of cellular features). These individual cell phenotypes are subsequently used to (iv) parameterize the prediction model and to simulate potential tumor progression. Model outcomes will be used to (v) assess the relative importance of the identified predictors in tumor invasiveness, in particular the microenvironmental factors. These predictors will be subsequently verified using (vi) an independent set.

Such a cross-disciplinary approach has an advantage over a more typical single laboratory research strategy since it will enables an analysis of a subject of an investigation from many different angles (i.e. breast vs. lung and also vessel vs. inflammation), and will lead to knowledge integration and cross-validation of our results.

Pathology Case Review, Analysis and Prediction

Figure 17:
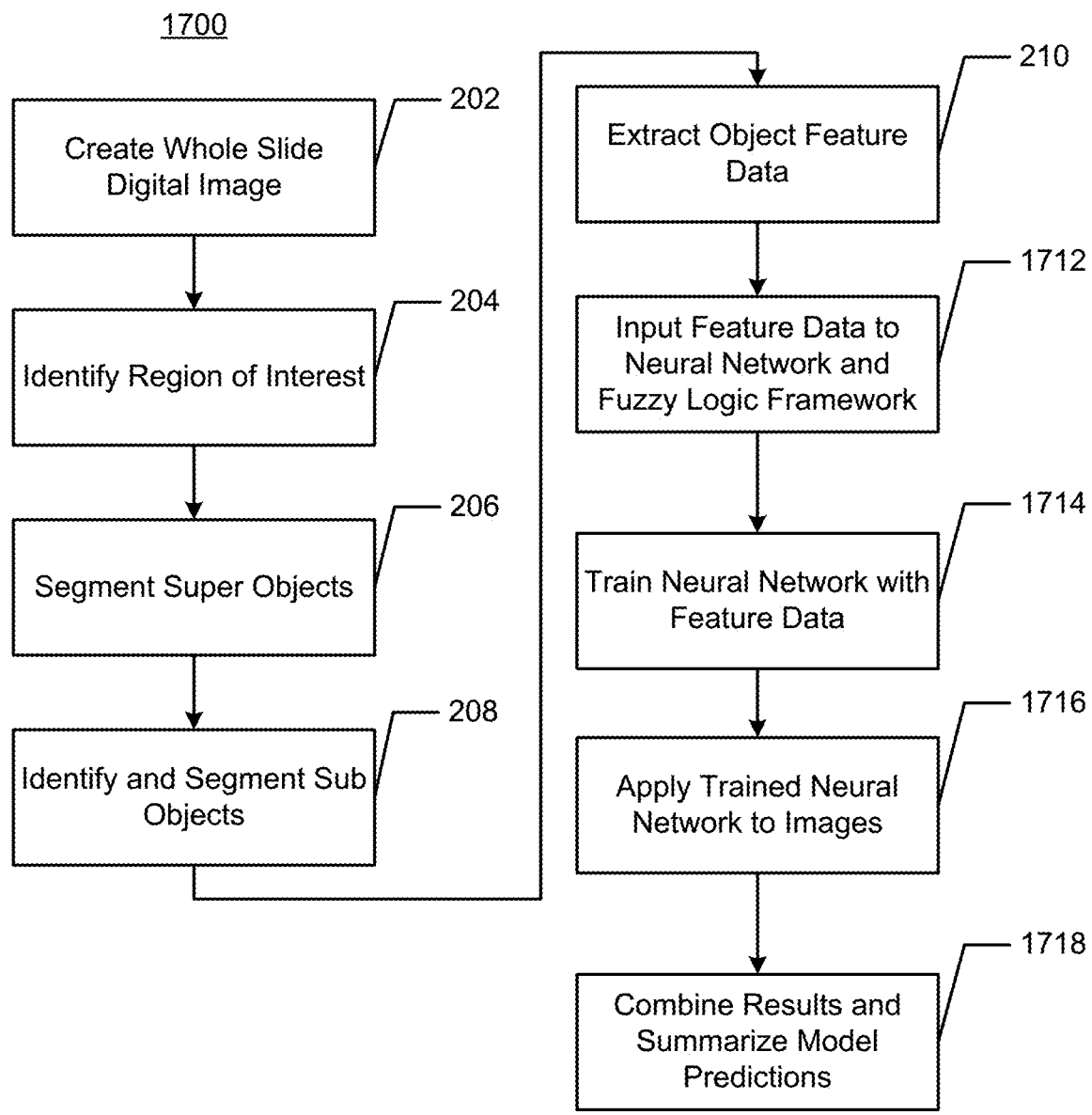
FIG. 17 illustrates an example operational flow.

FIG. 17 illustrates an example operational flow 1700 in accordance with present disclosure wherein visualizations of features of digital images are generated from image data. As will be described below, using digitized slides, cell feature data may used to predict outcomes. In the operational flow 1700, steps 202-210 are the same as described above and will not be repeated herein below.

At 1712, the feature data may be input to a neural network and/or fuzzy logic framework. Neural networks are an information processing paradigm that is inspired by the way biological nervous systems, such as the brain, process information. The key element of this paradigm is the novel structure of the information processing system. It is composed of a large number of highly interconnected processing elements (neurons) working in unison to solve specific problems. Thus, neural networks can learn by example. Typically, a neural network is configured for a specific application, such as pattern recognition or data classification, through a learning process. Learning in biological systems involves adjustments to the synaptic connections that exist between the neurons.

"Fuzzy logic" comes from the theory of fuzzy sets. Fuzzy logic is an approach to computing based on "degrees of truth" rather than the usual "true or false" (1 or 0) Boolean logic. A fuzzy subset A of a set X is characterized by assigning to each element x of X the degree of membership of x in A. As such, if X is a set of propositions then its elements may be assigned their degree of truth, which may be "absolutely true," "absolutely false" or some intermediate truth degree: a proposition may be more true than another proposition.

At 1714, the neural network and/or fuzzy logic framework is trained based on the feature data to determine best outcomes. The training may determine what feature or combination of features are most relevant. Within the feature data, multiple layers/combinations of features may be applied to see how well the combinations predict outputs. The training attempts to learn most the robust or effective way to make accurate prediction, which can be applied to image (at 1716). As such, the feature data can be used to learn and make predictions (at 1718).

Thus, the above operational flow presents a method by which feature data can be extracted from a digitized image and classified using neural networks to predict outcomes.

Figure 18:
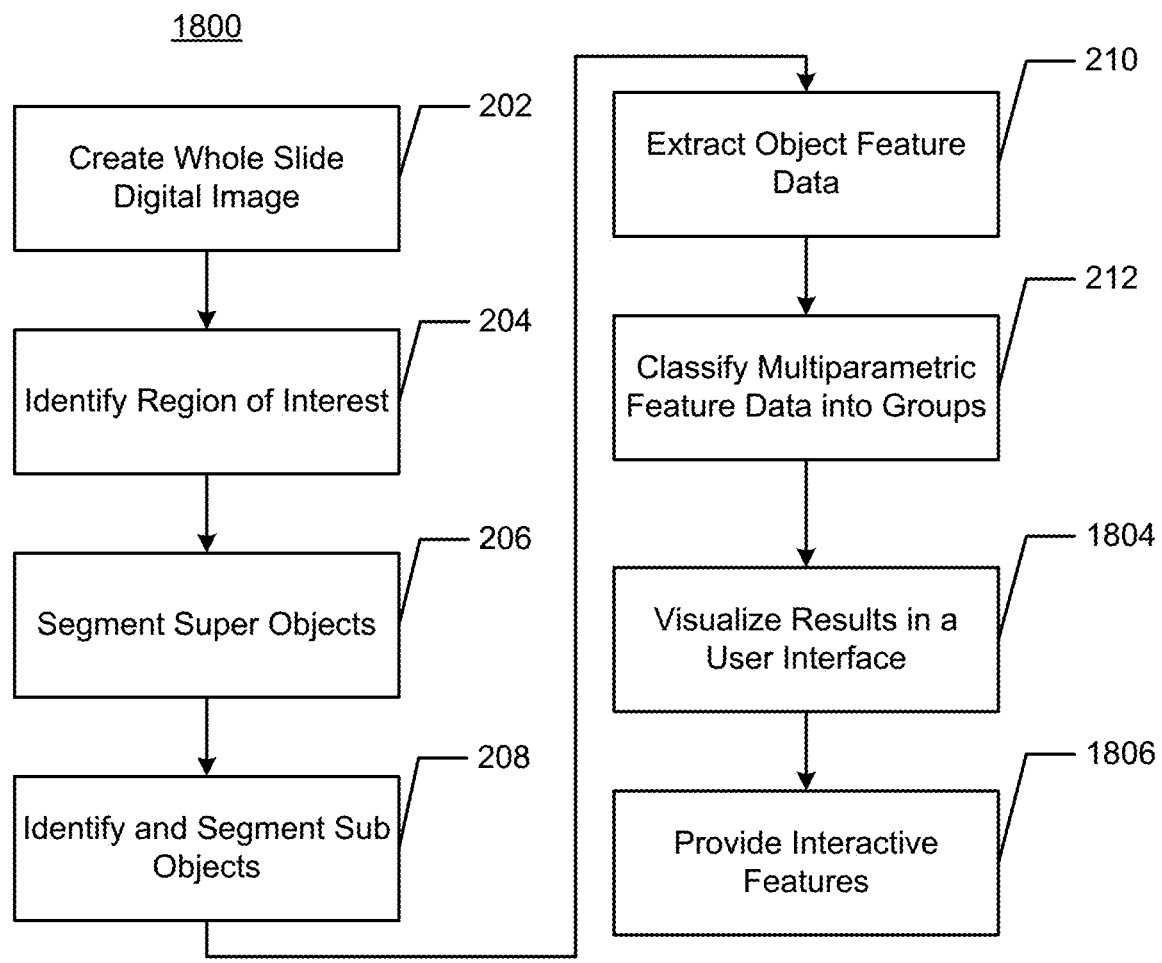
FIG. 18 illustrates another example operational flow.

FIG. 18 illustrates an example operational flow 1800 in accordance with present disclosure wherein visualizations of features of digital images are generated from image data. As will be described below, using digitized slides, cell feature data may be identified and displayed to provide a visualization of certain characteristics of tumor cells. The visualizations may be interactive to receive and process user inputs.

Figure 19:
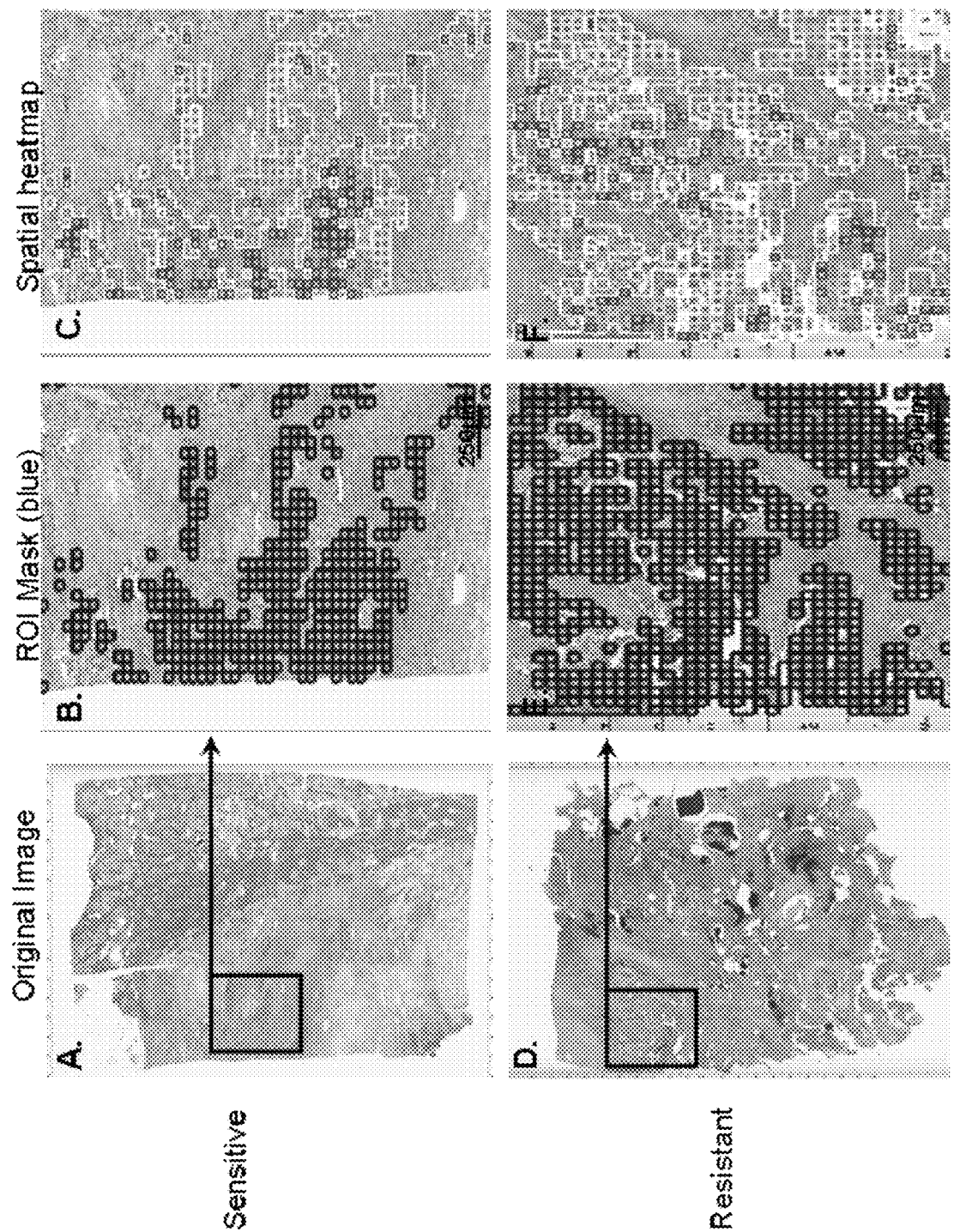
FIG. 19 illustrates visualizations associated with the operational flows of FIGS. 17-18.

In the operational flow 1800, steps 202-212 are the same as described above and will not be repeated herein below. At 1804, the group(s) are displayed. For example, with reference to FIG. 19C and FIG. 19F, a visualization is presented that codes cells within a particular group by, e.g., color. In the visualization, colored squares are provided where each square represents, e.g., a few hundred cells. The visualization graphically presents area of the data that is of interest. For example, areas in blue may be areas where a tumor exits. Thus, the visualization is a heat map showing a display of where the particular classifications defined at 1804 exist. The heat map in the example of FIGS. 19C and 19F show that features in green and read are more heterogeneous in the resistant sample, whereas the features are more homogenous in the sensitive sample.

Figure 20:
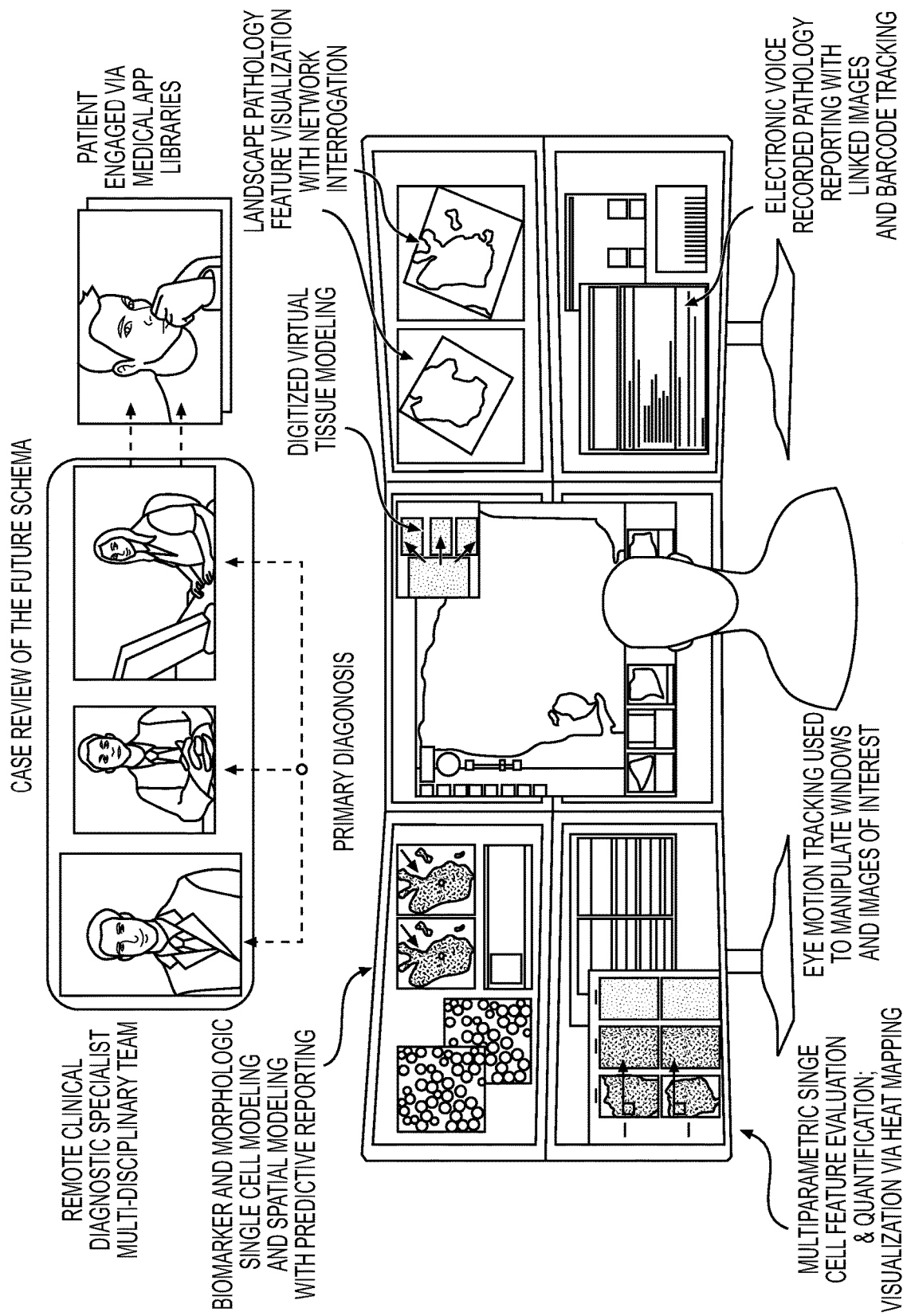
FIG. 20 illustrates an example user interface.

In accordance with aspects of the disclosure, at 1806, areas in the visualization may receive user inputs to alter the visualization. For example, a user may alter the views, metrics, scales, features, objects to visualize a wide spectrum of data on monitor. The user interface interacts with feature data stored in the database such that metrics can be applied to visually interrogate the displayed sample. The user may interact with an interface such as shown in FIG. 20.

Thus, the above operational flow presents a method by which feature data can be classified and displayed visually.

FIG. 21 shows an exemplary computing environment in which example implementations and aspects may be implemented. The computing system environment is only one example of a suitable computing environment and is not intended to suggest any limitation as to the scope of use or functionality.

Numerous other general purpose or special purpose computing system environments or configurations may be used. Examples of well known computing systems, environments, and/or configurations that may be suitable for use include, but are not limited to, personal computers (PCs), server computers, handheld or laptop devices, multiprocessor systems, microprocessor-based systems, network PCs, minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that performs particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

An exemplary system for implementing aspects described herein includes a computing device, such as computing device 2100. In its most basic configuration, computing device 2100 typically includes at least one processing unit 2102 and memory 2104. Depending on the exact configuration and type of computing device, memory 2104 may be volatile (such as random access memory (RAM)), non-volatile (such as read-only memory (ROM), flash memory, etc.), or some combination of the two. This most basic configuration is illustrated in FIG. 21 by dashed line 2106.

Computing device 2100 may have additional features/functionality. For example, computing device 2100 may include additional storage (removable and/or non-removable) including, but not limited to, magnetic or optical disks or tape. Such additional storage is illustrated in FIG. 2100 by removable storage 2108 and non-removable storage 2110.

Computing device 2100 typically includes a variety of computer readable media. Computer readable media can be any available media that can be accessed by device 2100 and include both volatile and non-volatile media, and removable and non-removable media.

Computer storage media include volatile and non-volatile, and removable and non-removable media implemented in any method or technology for storage of information such as computer readable instructions, data structures, program modules or other data. Memory 2104, removable storage 2108, and non-removable storage 2110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2100. Any such computer storage media may be part of computing device 2100.

Computing device 2100 may contain communications connection(s) 2112 that allow the device to communicate with other devices. Computing device 2100 may also have input device(s) 2114 such as a keyboard, mouse, pen, voice input device, touch input device, etc. Output device(s) 2116 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the processes and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be affected across a plurality of devices. Such devices might include PCs, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method of simulating tumor characteristics over time, comprising:
   obtaining digital slide image data of a tissue;
   identifying regions of interest in the digital slide image data by performing a multidimensional statistical and morphometrical analysis to the digital slide image data to identify quantitative features of individual cells that are characteristic of specific tumors;
   extracting object feature data from objects of interest, wherein the feature data represents parameters associated with the objects;
   reconstructing 3D tissue architecture and metabolic landscape from object of interest identified in separate but consecutive tissue slices;
   building a model space and parameterizing each object of interest; and
   simulating the tissue over time in accordance with the object feature data.

2. The method of claim 1, wherein identifying the regions of interest includes segmenting non-tumor regions from tumor regions.

3. The method of claim 1, further comprising applying a spatial prediction modeling that is parameterized from histological feature data obtained from the slide image data.

4. The method of claim 1, further comprising:
   quantitatively classifying multidimensionality and heterogeneity of image-based data;
   correlating results of the classifying with patient survival outcome data; and
   determining a set of cellular features that distinguish between tumors that led to recurrence or metastasis from tumors that did not progress.

5. The method of claim 1, further comprising reconstructing a tissue metabolic landscape by utilizing information from consecutive tissue slices to determine levels of different metabolites simultaneously in each region of the tissue.

6. The method of claim 1, further comprising testing dynamical interactions between tumor cells, a microenvironment of the tumor cells and treatment of the tumor cells.

7. The method of claim 6, further comprising generating dynamic simulations of at least one of a history a particular tumor prior to resection, a future progression of the particular tumor, and response of the particular tumor to therapeutic treatments.

8. The method of claim 1, further comprising:
   using a whole tumor tissue and a surrounding stroma after tumor resection together with a panel of molecular biomarkers; and
   providing an analysis of a morphological and metabolic state of the whole tumor.

9. The method of claim 1, further comprising combining static information from pathology samples with dynamical 2D/3D computer simulations using a computer model parameterized with individual patient data.

10. The method of claim 1, further comprising applying a multidimensional statistical and morphometrical analysis to identify quantitative features of individual cells that are characteristic for a given tumor type, grade, stage or hormonal status.

11. A method of virtual pathology simulation, comprising:
    using a model parameterization with patient-specific tumor morphology;
    characterizing individual cellular features of each type of tumor;
    simulating each tissue by systematically varying parameters defining cell doubling time, metabolic state and sensitivity to therapeutic compounds, wherein the model produces multi-parameter report charts of tumor response to a typical treatment schedule; and
    analyzing outcomes produced by the model,
    wherein the patient-specific tumor morphology includes at least one of a localization of tumor vasculature, localization of proliferating cells and regions of tumor hypoxia and tumor cells glycolytic state.

12. The method of claim 11, further comprising accounting for tumor and stromal cell's morphometric parameters and expression levels of molecular biomarkers to provide a prediction of optimal tumor response.

13. A method of landscape pathology, comprising:
    obtaining a slide image data of a tissue;
    identifying regions of interest in the slide image data;
    segmenting objects of interest in the slide image data;
    extracting object feature data that represents parameters associated with each object of interest;
    performing analytics on multiparametric tissue properties to determine environmental factors leading to tumor growth;
    creating a multidimensional visualization of cell distributions in accordance with the object feature data;
    quantifying heterogeneities within the cell distributions;
    applying a topographical analysis of spatial heterogeneity; and determining at least one of spatial pattern including point patterns, spatial patterns, network patterns and outlier patterns.

14. The method of claim 13, wherein the regions of interest are non-tumor regions that are segmented from tumor regions.

15. The method of claim 13, further comprising:
identifying patterns in the objects of interest using landscape ecology and connectivity; and
applying an outlier analysis to determine biological relationships in cellular distributions within the objects of interest.

16. The method of claim 13, further comprising:
using one of a number of interactions with neighbors in a nearest neighbor analysis, a buffered analysis and a spatial autocorrelation to discern morphological or other similarities between nearby individuals; and
determining a size and connectivity of pockets of cells with distinct morphologies.

17. The method of claim 13, further comprising measuring environmental factors that lead to tumor growth to quantify a microenvironment.

18. The method of claim 13, further comprising extracting Darwinian interactions of environmental and cellular adaptations from the slide image data.

19. The method of claim 13, wherein the spatial patterns are determined in accordance with clustered patterns.

20. The method of claim 13, wherein a hill-and-valley map is used to show spatial distribution.

* * * * *